United States Patent
Westbrook

(10) Patent No.: US 10,751,389 B2
(45) Date of Patent: *Aug. 25, 2020

(54) THERAPEUTIC USE OF P75NTR NEUROTROPHIN BINDING PROTEIN

(71) Applicant: Levicept LTD, London (GB)

(72) Inventor: Simon Westbrook, London (GB)

(73) Assignee: Levicept LLD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/680,872

(22) Filed: Aug. 18, 2017

(65) Prior Publication Data

US 2018/0161392 A1 Jun. 14, 2018

Related U.S. Application Data

(62) Division of application No. 14/384,302, filed as application No. PCT/GB2013/050632 on Mar. 14, 2013, now Pat. No. 9,764,000.

(60) Provisional application No. 61/610,682, filed on Mar. 14, 2012.

(51) Int. Cl.

| | | |
|---|---|---|
| A61K 38/00 | (2006.01) | |
| A61K 38/10 | (2006.01) | |
| A61K 38/16 | (2006.01) | |
| C07K 14/705 | (2006.01) | |
| C07K 14/48 | (2006.01) | |
| C07K 14/71 | (2006.01) | |
| C07K 14/76 | (2006.01) | |
| C07K 14/79 | (2006.01) | |
| A61K 38/17 | (2006.01) | |
| A61K 47/68 | (2017.01) | |
| A61K 47/60 | (2017.01) | |
| A61K 47/64 | (2017.01) | |
| A61K 47/66 | (2017.01) | |
| A61K 38/19 | (2006.01) | |
| A61K 45/06 | (2006.01) | |
| C07K 16/22 | (2006.01) | |
| A61K 48/00 | (2006.01) | |

(52) U.S. Cl.
CPC ............ *A61K 38/179* (2013.01); *A61K 38/10* (2013.01); *A61K 38/191* (2013.01); *A61K 45/06* (2013.01); *A61K 47/60* (2017.08); *A61K 47/64* (2017.08); *A61K 47/643* (2017.08); *A61K 47/644* (2017.08); *A61K 47/66* (2017.08); *A61K 47/6803* (2017.08); *A61K 47/6811* (2017.08); *C07K 14/48* (2013.01); *C07K 14/70578* (2013.01); *C07K 14/71* (2013.01); *C07K 14/76* (2013.01); *C07K 14/79* (2013.01); *C07K 16/22* (2013.01); *A61K 48/00* (2013.01); *A61K 48/005* (2013.01); *C07K 2317/76* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 8,669,350 B2 | 3/2014 | Chou |
| 9,764,000 B2 | 9/2017 | Westbrook |
| 9,873,728 B2 | 1/2018 | Westbrook |
| 2007/0243132 A1 | 10/2007 | Russell-Jones |
| 2008/0182978 A1 | 7/2008 | Rosenthal |
| 2009/0232808 A1 | 9/2009 | Priest |
| 2010/0061981 A1 | 3/2010 | O'Leary |
| 2011/0014208 A1 | 1/2011 | MacDonald |
| 2013/0164286 A1 | 6/2013 | Chou |
| 2014/0017235 A1 | 1/2014 | Rosenthal |
| 2017/0204156 A1 | 7/2017 | Westbrook |
| 2018/0170995 A1 | 6/2018 | Westbrook |
| 2018/0273603 A1 | 9/2018 | Westbrook |

FOREIGN PATENT DOCUMENTS

| | | |
|---|---|---|
| CN | 102233128 | 11/2011 |
| CN | 102586313 | 7/2012 |
| WO | 9207076 | 4/1992 |
| WO | 2005037867 | 7/2005 |
| WO | 2006079176 | 8/2006 |
| WO | 2007026567 | 3/2007 |
| WO | 2012101664 | 8/2012 |
| WO | 2013136078 | 9/2013 |
| WO | 2015040398 | 3/2015 |
| WO | 2016009222 | 1/2016 |
| WO | 2016146841 | 9/2016 |

OTHER PUBLICATIONS

Wells, James A. (1990). Additivity of Mutational Effects in Proteins. Biochemistry. 29(37):8509-8517.

Ngo, J. et al., (1994). Computational Complexity, Protein Structure Prediction and Levinthal Paradox. In Mers and Le Grand (Eds.) The Protein Folding Problem and Tertiary Structure Prediction. Birkhauser: Boston, pp. 491-495.

Pincheira, R. et al., "The Sall2 Transcription Factor is a Novel p75NTR Binding Protein that Promotes the Development and Functipn of Neurons," Ann. N.Y., Acad. Sci. 1144: 53-55 (2008).

(Continued)

*Primary Examiner* — Christine J Saoud
*Assistant Examiner* — Jon M Lockard
(74) *Attorney, Agent, or Firm* — Dennis A. Bennett; Stephanie M. Greer; Chris Marion

(57) ABSTRACT

The present invention relates to a p75NTR neurotrophin binding protein, p75NTR(NBP), for use in the treatment of pain and/or a symptom of pain.

13 Claims, 13 Drawing Sheets

Specification includes a Sequence Listing.

(56) References Cited

OTHER PUBLICATIONS

Iwakura, N. et al., "Role of Low-Affinity Nerve Growth Factor Receptor Inhibitory Antibody in Reducing Pain Behavior and Calcitonin Gene-Related Peptide Expression in a Rat Model of Wrist Joint Inflammatory Pain," Elsevier Science B.V., Amsterdam 35(2): 267-273 (2010).
Cell Signaling Technology, p75NTR Antibody #2693 (2010).
Fukui et al., "Low Affinity NCF Receptor (p75 Neurotrophin Receptor) Inhabitory Antibody Reduces Pain Behavior and CGRP Expression in DRG in the Mouse Sciatic Nerve Crush Model," Journal of Orthopaedic Research, vol. 28, No. 3, Mar. 2010, 6 pgs.
International Search Report and Written Opinion, PCT Application No. PCT/GB2013/050632, dated Jun. 6, 2013, 15 pgs.
Marler, K. et al., "Pro-Neurotrophins Secreted From Retinal Ganglion Cell Axons and Necessary for EphrinA-p75—Mediated Axon Guidance," Neural Development, vol. 5, No. 30, Nov. 2, 2010, 10 pgs.
T Hart, B. et al., "The Use of Animal Models to Investigate the Pathogenesis of Neuroinflammatory Disorders of the Central Nervous System", Curr Opin Neurol., 16(3):375-83, (2003).
Amet, N. et al., "Insertion of the Designed Helical Linker Led to Increased Expression of tf-Based Fusion Proteins", Pharm Res., 26(3):523-8, (2009).
Armour, K. et al., "Recombinant human IgG molecules lacking Fcgamma receptor I binding and monocyte triggering activities", Eur J Immunol., 29(8):2613-24, (1999).
Bai, Y. et al., "Recombinant Granulocyte Colony-Stimulating Factor-Transferrin Fusion Protein as an Oral Myelopoietic Agent", Proc Natl Acad Sci., 102(20):7292-6, (2005).
Barthel, C. et al., "Nerve Growth Factor and Receptor Expression in Rheumatoid Arthritis and Spondyloarthritis", Arthritis Res Ther., 11(3):R82, (2009).
Bothwell, M. et al., "Dissociation Equilibrium Constant of Beta Nerve Growth Factor", J Biol Chem., 252(23):8532-6, (1977).
Bowie, J. et al., "Deciphering the Message in Protein Sequences: Tolerance to Amino Acid Substitutions", Science, 247(4948):1306-10, (1990).
Burgess, W. et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J Cell Bio., 111:2129-38, (1990).
Chu, C. et al., "Mitochondrial Dependence of Nerve Growth Factor-Induced Mechanical Hyperalgesia", Pain, 152(8):1832-7, (2011).
Cirillo, G. et al., "Intrathecal NGF Administration Reduces Reactive Astrocytosis and Changes Neurotrophin Receptors Expression Pattern in a Rat Model of Neuropathic Pain", Cell Mol Neurobiol., 30(1):51-62, (2010).
Cowan, W., "Viktor Hamburger and Rita Levi-Montalcini: the Path to the Discovery of Nerve Growth Factor", Annu Rev Neurosci., 24:551-600, (2001).
Dray, A. et al., "Arthritis and Pain. Future Targets to Control Osteoarthritis Pain", Arthritis Research & Ther., 9(3): pp. 1-14, (2007).
EPO Preliminary Response and Claims Amendment, PCT/GB2014/052833, dated Jul. 20, 2015.
Fukui, Y. et al., "Low Affinity NGF Receptor (p75 Neurotrophin Receptor) Inhibitory Antibody Reduces Pain Behavior and CGRP Expression in DRG in the Mouse Sciatic Nerve Crush Model", J Orthop Res., 28(3):279-83, (2010).
Ghilardi, J. et al., "Sustained Blockade of Neurotrophin Receptors TrkA, TrkB and TrkC Reduces Non-Malignant Skeletal Pain but Not the Maintenance of Sensory and Sympathetic Nerve Fibers", Bone., 48(2):389-98, (2011).
Guo, J. et al., "proNGF inhibits proliferation and oligodendrogenesis of postnatal hippocampal neural stem/ progenitor cells through p 75NTR in vitro", Stem Cell Research, 11(2):874-87, (2013).

Harding, F. et al., "The Immunogenicity of Humanized and Fully Human Antibodies: Residual Immunogenicity Resides in the CDR Regions", MAbs, 2(3):256-65, (2010).
Hayashi, K. et al., "Involvement of NGF in the Rat Model of Persistent Muscle Pain Associated with Taut Band", J Pain, 12(10):1059-68, (2011).
He, X. et al., "Structure of Nerve Growth Factor Complexed with the Shared Neurotrophin Receptor p75", Science, 304(5672):870-5, (2004).
Huang, E. et al., "Trk Receptors: Roles in Neuronal Signal Transduction", Annu Rev Biochem., 72:609-42, (2003).
Ichim, G. et al., "Neurotrophins and Cell Death", Exp Cell Res., 318(11):1221-8, (2012).
International Application No. PCT/EP2016/056049; International Preliminary Report on Patentability, dated Sep. 19, 2017; 7 pages.
International Application No. PCT/EP2016/056049; International Search Report and Written Opinion of the International Searching Authority, dated May 23, 2016; 11 pages.
International Application No. PCT/GB2013/050632; International Preliminary Report on Patentability, dated Sep. 16, 2014; 9 pages.
International Application No. PCT/GB2014/052833; International Preliminary Report on Patentability, dated Sep. 18, 2015; 9 pages.
International Application No. PCT/GB2014/052833; International Search Report and Written Opinion of the International Searching Authority, dated Dec. 17, 2014; 9 pages.
International Application No. PCT/GB2015/052083; International Preliminary Report on Patentability, dated Jan. 17, 2017; 9 pages.
International Application No. PCT/GB2015/052083; International Search Report and Written Opinion of the International Searching Authority, dated Jan. 10, 2015; 13 pages.
Johnson, D. et al., "Expression and Structure of the Human NGF Receptor", Cell., 47(4):545-54, (1986).
Jung, K. et al., "Regulated Intramembrane Proteolysis of the P75 Neurotrophin Receptor Modulates its Association with the TrkA Receptor", J Biol Chem., 278(43):42161-9, (2003).
Kanning, C. et al., "Proteolytic Processing of the P75 Neurotrophin Receptor and Two Homologs Generates C-terminal Fragments with Signaling Capability", J Neurosci., 23(13):5425-36, (2003).
Kenchappa, R. et al., "P75 Neurotrophin Receptor-Mediated Apoptosis in Sympathetic Neurons Involves a Biphasic Activation of JNK and Up-Regulation of Tumor Necrosis Factor-Alpha-Converting Enzyme/ADAM17", J Biol Chem., 285(26):20358-68, (2010).
Lane, N. et al., "RN624 (Anti-NGF) Improves Pain and Function in Subjects with Moderate Knee Osteoarthritis: A Hhase I Study", Arthritis & Rheumatism, 52(9 Suppl.):S461, 3 pages, (2005).
McDonald, C. et al., "Targeting the Nogo Receptor Complex in Diseases of the Central Nervous System", Curr Med Chem., 18(2):234-44, (2011).
Orita, S. et al., "Inhibiting Nerve Growth Factor or its Receptors Downregulates Calcitonin Gene-Related Peptide Expression in Rat Lumbar Dorsal Root Ganglia Innervating Injured Intervertebral Discs", J Orthop Res., 28(12):1614-20, (2010).
Pawson, T. et al. "Assembly of Cell Regulatory Systems Through Protein Interaction Domains", Science, 300:445-52, (2003).
Pezet, S. et al., "Differential Regulation of NGF Receptors in Primary Sensory Neurons by Adjuvant-Induced Arthritis in the Rat", Pain, 90(1-2):113-25, (2001).
Rabizadeh, S. et al., "Induction of Apoptosis by the Low-Affinity NGF Receptor", Science, 261(5119):345-8, (1993).
Radeke, M. et al., "Gene Transfer and Molecular Cloning of the Rat Nerve Growth Factor Receptor", Nature, 325(6105):593-7, (1987).
Raychaudhuri, S. et al., "Nerve Growth Factor: A key Local Regulator in the Pathogenesis of Inflammatory Arthritis", Arthritis Rheum., 63(11):3243-52, (2011).
Stas, P. et al., "Immunogenicity Assessment of Antibody Therapeutics", Recombinant Antibodies for Immunotherapy, Ch. 2:20-43, (2009).
Svensson, P. et al., "Human Nerve Growth Factor Sensitizes Masseter Muscle Nociceptors in Female Rats", Pain, 148(3):473-80, (2010).
Tria, M. et al., "Pharmacokinetics of Nerve Growth Factor (NGF) Following Different Routes of Administration to Adult Rats", Exp Neurol., 127(2):178-83, (1994).

(56) References Cited

OTHER PUBLICATIONS

Truzzi, F. et al., "P75 Neurotrophin Receptor Mediates Apoptosis in Transit-Amplifying Cells and its Overexpression Restores Cell Death in Psoriatic Keratinocytes", Cell Death Differ, 18(6):948-58, (2011).
U.S. Appl. No. 14/384,302; Examiner-Initiated Interview Summary, dated May 18, 2017; 1 page.
U.S. Appl. No. 14/384,302; Notice of Allowance, dated May 18, 2017; 9 pages.
U.S. Appl. No. 15/022,505; Examiner-Initiated Interview Summary, dated Sep. 15, 2017; 1 page.
U.S. Appl. No. 15/022,505; Non-Final Office Action, dated Jan. 30, 2017; 37 pages.
U.S. Appl. No. 15/022,505; Notice of Allowance, dated Sep. 15, 2017; 10 pages.
U.S. Appl. No. 15/326,936; Non-Final Office Action, dated Dec. 5, 2018; 17 pages.
U.S. Appl. No. 15/559,368; Non-Final Office Action, dated Nov. 30, 2018; 26 pages.
U.S. Appl. No. 15/559,368; Notice of Allowance, dated Feb. 6, 2020; 19 pages.
U.S. Appl. No. 15/844,022; Non-Final Office Action, dated Dec. 14, 2018; 32 pages.
Ueda, K. et al., "Local Administration of a Synthetic Cell-Penetrating Peptide Antagonizing TrkA Function Suppresses Inflammatory Pain in Rats", J Pharmacol Sci., 112(4):438-43, (2010).
Vilar, M. et al., "Activation of the p 75 neurotrophin receptor through conformational rearrangement of disulphide-linked eceptor dimers", Neuron., 62(1):72-83, (2009).
Vilar, M. et al., "Ligand-Independent Signaling by Disulfide-Crosslinked Dimers of the p75 Neurotrophin Receptor", J Cell Sci., 122(Pt 18):3351-7, (2009).
Wang, Yong-Tang et al., "Ameliorative Effects of p75NTR-ED-Fc on Axonal Regeneration and Functional Recovery in Spinal Cord-Injured Rats," Molecular Neurobiology, Humana Press, US, 52(3):1821-34, (2014).
Watanabe, T. et al., "The P75 Receptor is Associated with Inflammatory Thermal Hypersensitivity", J Neurosci Res., 86(16):3566-74, (2008).
Yamaoka, J. et al., "Changes in cutaneous sensory nerve fibers induced by skin-scratching in mice", J Dermatol Sci., 46(1):41-51, (2007).
Zampieri, N. et al. "Cleavage of p75 Neurotrophin Receptor by Alpha-Secretase and Gamma-Secretase Requires Specific Receptor Domains", J Biol Chem., 280(15):14563-71, (2005).
Zhao, H. et al., "Increasing the Homogeneity, Stability and Activity of Human Serum Albumin and Interferon-Alpha2b Fusion Protein by Linker Engineering", Protein Expr Purif., 61(1):73-7, (2008).

Figure 1 - p75NTR extracellular domain sequence, neurotrophin binding domains highlighted in bold

```
  1   MGAGATGRAM DGPRLLLLLL LGVSLGGAKE ACPTGLYTHS GECCKACNLG
 51   EGVAQPCGAN QTVCEPCLDS VTFSDVVSAT EPCKPCTECV GLQSMSAPCV
101   EADDAVCRCA YGYYQDETTG RCEACRVCEA GSGLVFSCQD KQNTVCEECP
151   DGTYSDEANH VDPCLPCTVC EDTERQLREC TRWADAECEE IPGRWITRST
201   PPEGSDSTAP STQEPEAPPE QDLIASTVAG VVTTVMGSSQ PVVTRGTTDN
251   LIPVYCSILA AVVVGLVAYI AFKRWNSCKQ NKQGANSRPV NQTPPPEGEK
301   LHSDSGISVD SQSLHDQQPH TQTASGQALK GDGGLYSSLP PAKREEVEKL
351   LNGSAGDTWR HLAGELGYQP EHIDSFTHEA CPVRALLASW ATQDSATLDA
401   LLAALRRIQR ADLVESLCSE STATSPV
```

Figure 2 [a] - Peptides identified by LCMS / MS of a p75NTR-Fc chimera, standard digest
[a] Detection of p75NTR extracellular domain standard
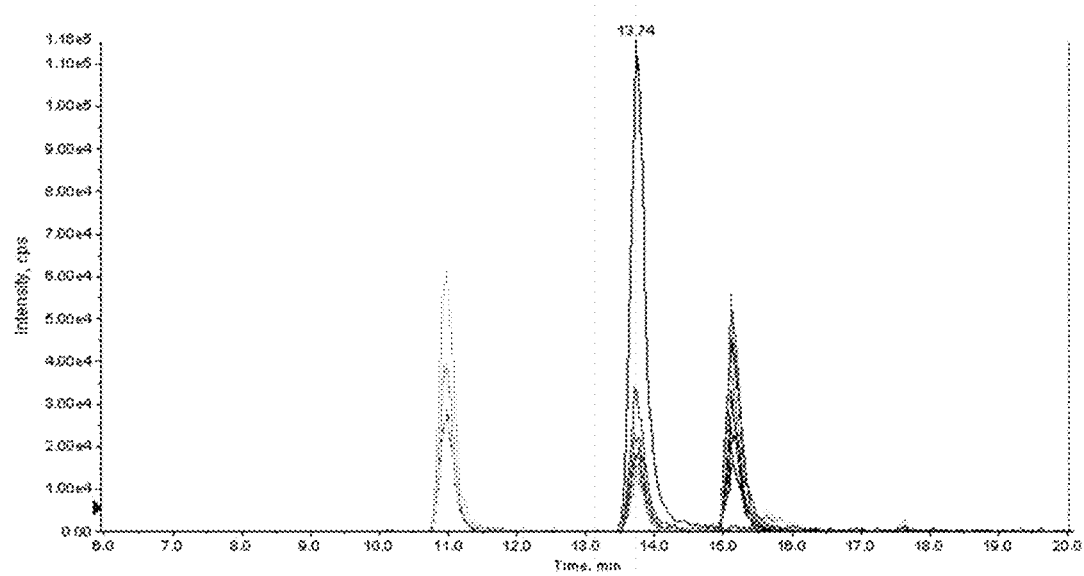
Peak at 11.0 min = CAYGYYQDETTGR
Peak at 13.74 min = WADAECEEIPGR
Peak at 15.2 min = VCEAGSGLVFSCQDK

Figure 2 [b] - Peptides identified by LCMS / MS of a p75NTR-Fc chimera, standard digest
[b] Detection of p75 extracellular domain from total NGF assay using commercial human serum
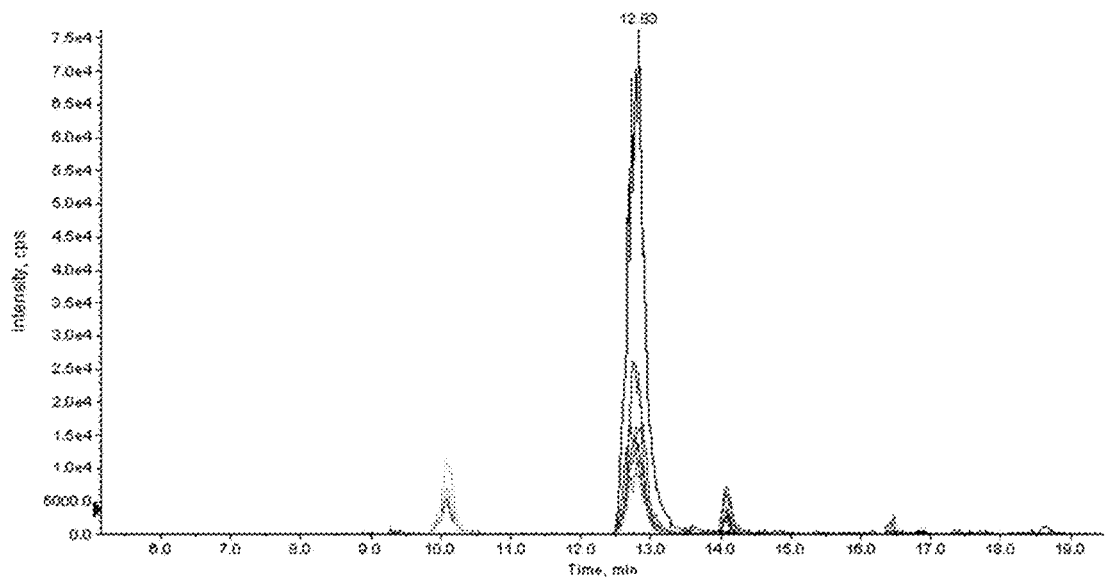
Peak at 10.0 min = CAYGYYQDETTGR
Peak at 12.83 min = WADAECEEIPGR
Peak at 14.2 min = VCEAGSGLVFSCQDK Figure 3. MS/MS sequence confirmation of the WADAECEEIPGR peak shown in Figure 2.
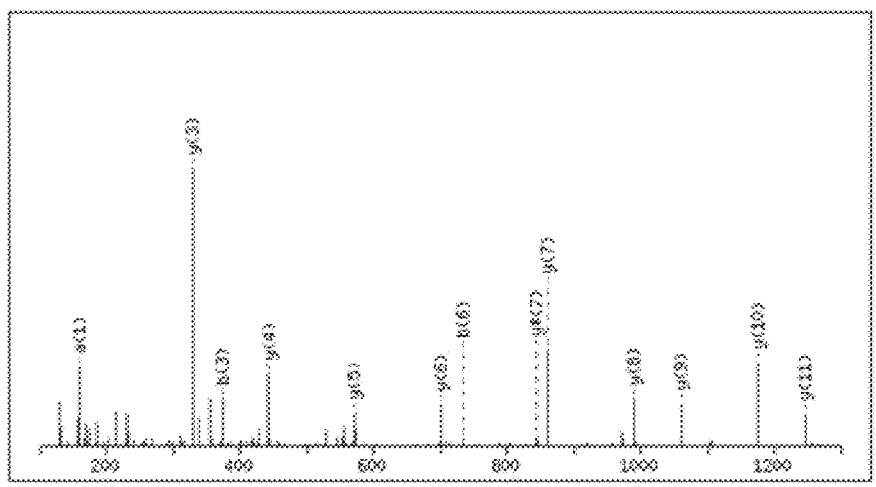
Monoisotopic mass of neutral peptide Mr(calc): 1431.61
Fixed modifications: Carbamidomethyl (C)
Ions Score: 94  Expect: 6.4e-007
Matches (Bold Red): 13/88 fragment ions using 14 most intense peaks
| # | a | a++ | b | b++ | Seq | y | y++ | y* | y*++ | # |
|---|---|---|---|---|---|---|---|---|---|---|
| 1 | 159.09 | 80.05 | 187.09 | 94.05 | W | | | | | 12 |
| 2 | 230.13 | 115.57 | 258.12 | 129.57 | A | 1246.54 | 623.77 | 1229.51 | 615.26 | 11 |
| 3 | 345.16 | 173.08 | 373.15 | 187.08 | D | 1175.50 | 588.25 | 1158.47 | 579.74 | 10 |
| 4 | 416.19 | 208.60 | 444.19 | 222.60 | A | 1060.47 | 530.74 | 1043.45 | 522.23 | 9 |
| 5 | 545.24 | 273.12 | 573.23 | 287.12 | E | 989.44 | 495.22 | 972.41 | 486.71 | 8 |
| 6 | 705.27 | 353.14 | 733.26 | 367.13 | C | 860.39 | 430.70 | 843.37 | 422.19 | 7 |
| 7 | 834.31 | 417.66 | 862.30 | 431.66 | E | 700.36 | 350.68 | 683.34 | 342.17 | 6 |
| 8 | 963.35 | 482.18 | 991.35 | 496.18 | E | 571.32 | 286.16 | 554.29 | 277.65 | 5 |
| 9 | 1076.44 | 538.72 | 1104.43 | 552.72 | I | 442.28 | 221.64 | 425.25 | 213.13 | 4 |
| 10 | 1173.49 | 587.25 | 1201.48 | 601.25 | P | 329.19 | 165.10 | 312.17 | 156.59 | 3 |
| 11 | 1230.51 | 615.76 | 1258.50 | 629.76 | G | 232.14 | 116.57 | 215.11 | 108.06 | 2 |
| 12 | | | | | R | 175.12 | 88.06 | 158.09 | 79.55 | 1 |

Figure 4 - p75NTR(NBP) inhibits NGF function in U2OS cell line expressing TrkA and in U2OS cell line co-expressing TrkA and p75NTR.
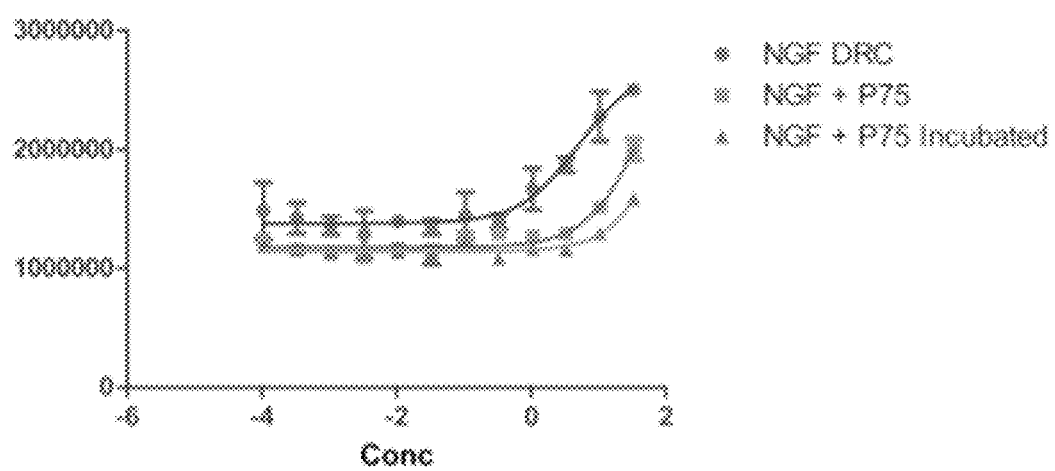
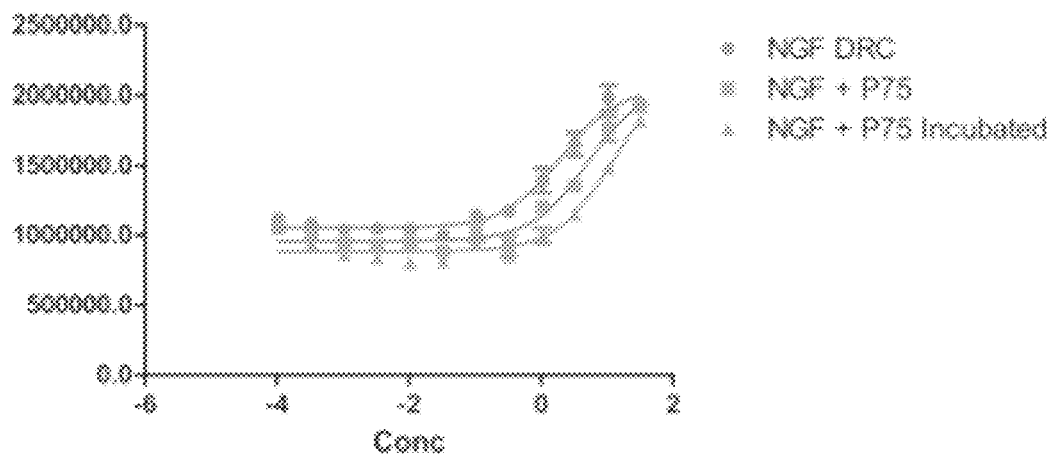

Figure 5 - Soluble p75NTR(NBP) inhibits BDNF function in U2OS cell line expressing TrkA and in U2OS cell line co-expressing TrkA and p75NTR.
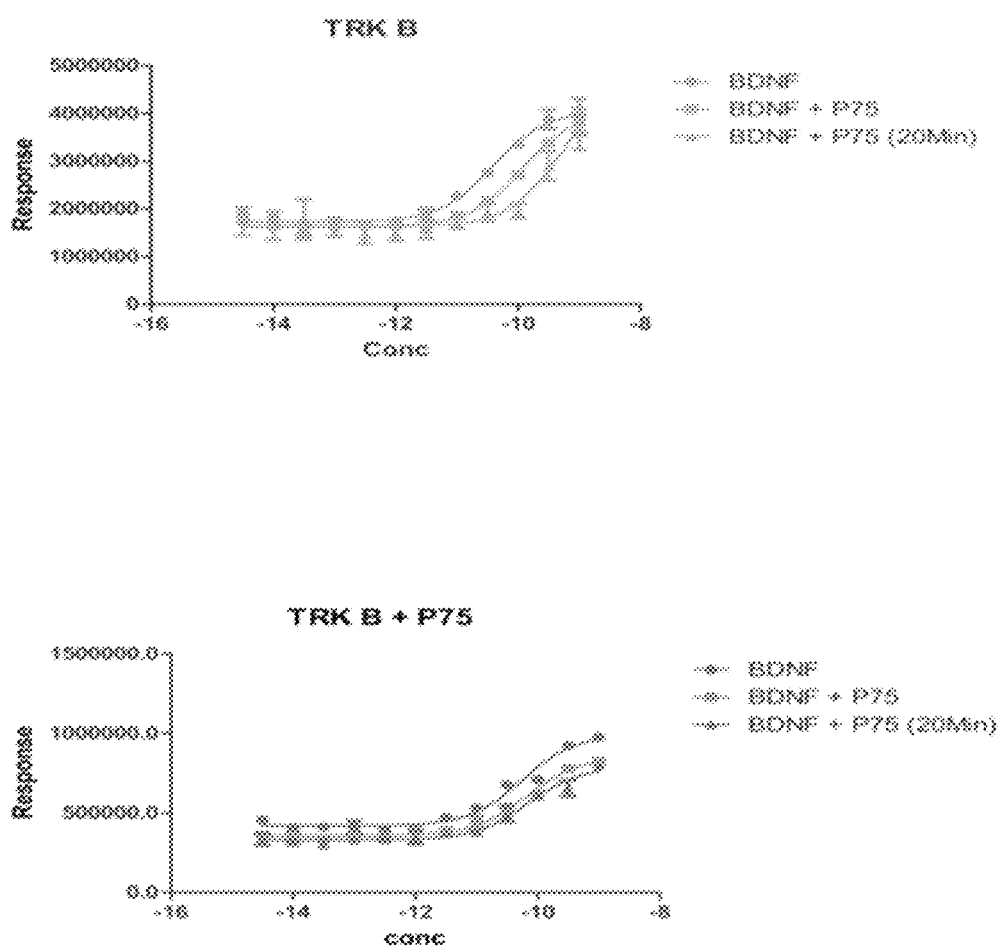

Figure 6 - Biocore data demonstrating p75NTR(NBP) binding to BDNF and competition between anti-BDNF and p75NTR(NBP)
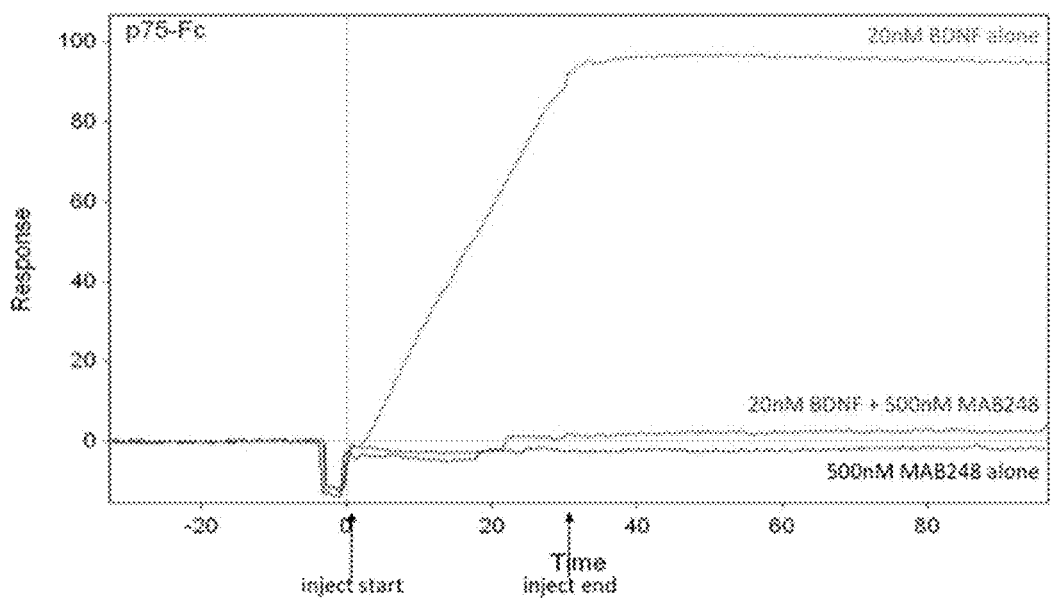

Figure 7– p75NTR(NBP) inhibition of NGF activity in PC12 cells
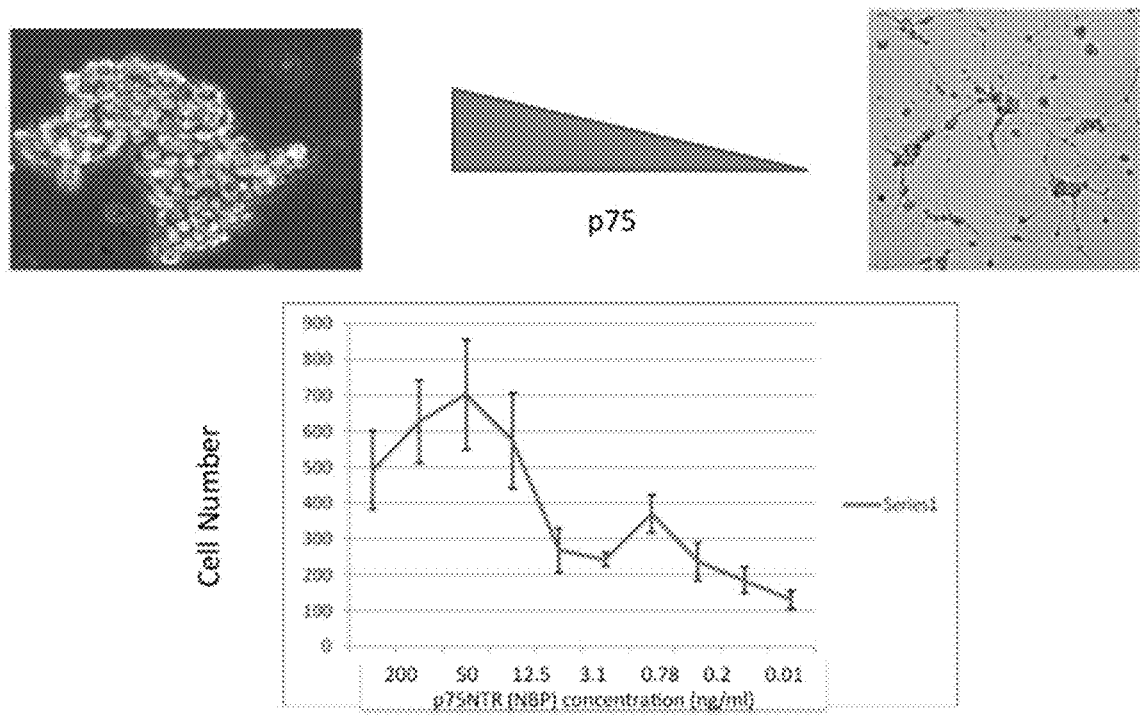

Figure 8 - p75NTR(NBP) inhibits BDNF pain effect in a model of nerve excitability
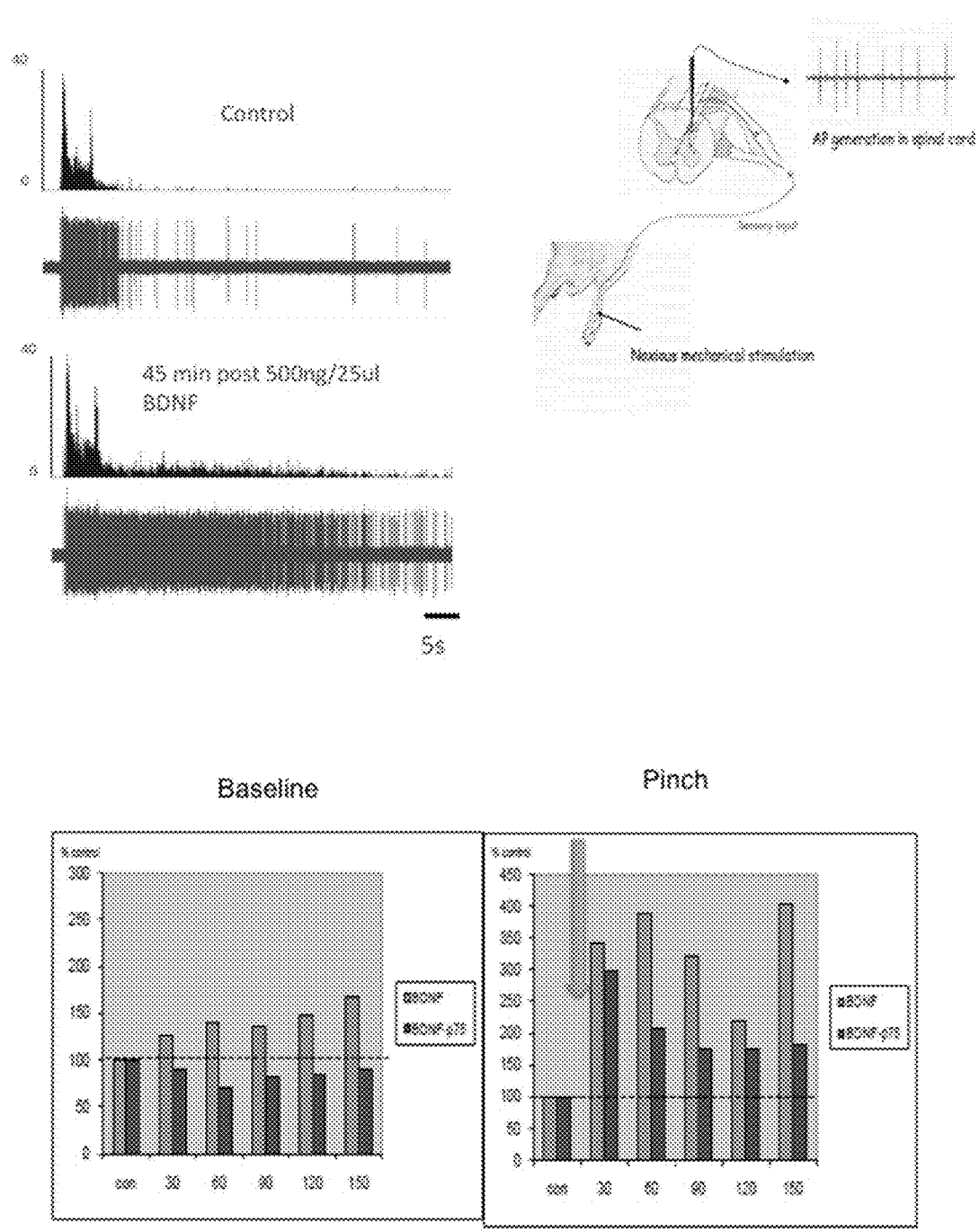

Figure 9 - Neurotrophin Binding Protein p75NTR(NBP) inhibits hyperalgesia in UVIH model
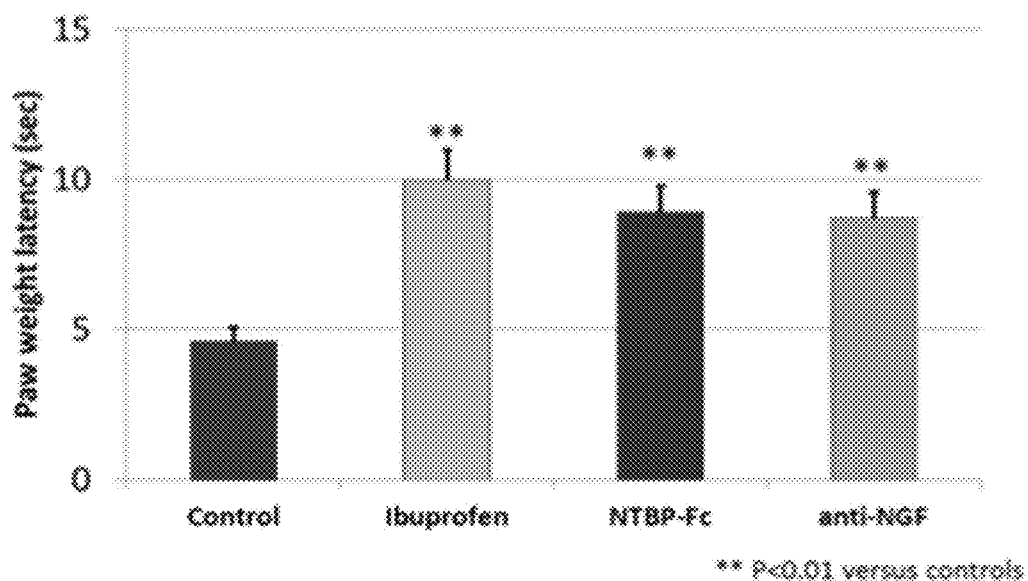

Figure 10 – SEQ ID NO. 1 Human p75NTR full amino acid sequence

```
  1  mgagatgram dgprllllll lgvslggake acptglyths gecckacnlg egvaqpcgan
 61  qtvcepclds vtfsdvvsat epckpctecv glqsmsapcv eaddavcrca ygyyqdettg
121  rceacrvcea gsglvfscqd kqntvceecp dgtysdeanh vdpclpctvc edterqlrec
181  trwadaecee ipgrwitrst ppegsdstap stqepeappe qdliastvag vvttvmgssq
241  pvvtrgttdn lipvycsila avvvglvayi afkrwnsckq nkqgansrpv nqtpppegek
301  lhsdsgisvd sqslhdqqph tqtasgqalk gdgglysslp pakreevekl lngsagdtwr
361  hlagelgyqp ehidsfthea cpvrallasw atqdsatlda llaalrriqr adlveslcse
421  statspv
```

Figure 11 - SEQ ID NO. 2 Human p75NTR extracellular domain including signal sequence

```
  1  mgagatgram dgprllllll lgvslggake acptglyths gecckacnlg egvaqpcgan
 61  qtvcepclds vtfsdvvsat epckpctecv glqsmsapcv eaddavcrca ygyyqdettg
121  rceacrvcea gsglvfscqd kqntvceecp dgtysdeanh vdpclpctvc edterqlrec
181  trwadaecee ipgrwitrst ppegsdstap stqepeappe qdliastvag vvttvmgssq
241  pvvtrgttdn
```

Figure 12 - SEQ ID NO. 3 Human p75NTR extracellular domain without signal sequence

```
ke acptglyths gecckacnlg egvaqpcgan qtvcepclds vtfsdvvsat epckpctecv
glqsmsapcv eaddavcrca ygyyqdettg rceacrvcea gsglvfscqd kqntvceecp gtysdeanh
vdpclpctvc edterqlrec trwadaecee ipgrwitrst ppegsdstap stqepeappe
qdliastvag vvttvmgssq pvvtrgttdn
```

Figure 13 SEQ ID NO. 4 Human p75NTR(NBP) neurotrophin binding domain 1
CAYGYYQDETTGR

Figure 14 SEQ ID NO. 5 Human p75NTR(NBP) neurotrophin binding domain 2
VCEAGSGLVFSCQD KQNTVCEECP GGTYSDEANH VDPCLPCTVCEDTER

Figure 15 SEQ ID NO.6 Human p75NTR(NBP) neurotrophin binding domain 3
VCEAGSGLVFSCQDK

Figure 16 SEQ ID NO. 7 Human p75NTR(NBP) neurotrophin binding domain 4
WADAECEEIPGR

Figure 17 SEQ ID NO. 8 Human p75NTR(NBP) neurotrophin binding domain 5
LDSVTSDVVSATEPCKP

Figure 18 SEQ ID NO. 9 Human Transferrin

```
  1  mrlavgallv cavlglclav pdktvrwcav seheatkcqs frdhmksvip sdgpsvacvk
 61  kasyldcira iaaneadavt ldaglvyday lapnnlkpvv aefygskedp qtfyyavavv
121  kkdsgfqmnq lrgkkschtg lgrsaqwnip igllycdlpe prkplekava nffsgscapc
181  adgtdfpqlc qlcpgcgcst lnqyfgysga fkclkdgagd vafvkhstif enlankadrd
241  qyellcldnt rkpvdeykdc hlaqvpshtv varsmggked liwellnqaq ehfgkdkske
301  fqlfssphgk dllfkdsahg flkvpprmda kmylgyeyvt airnlregtc peaptdeckp
361  vkwcalshhe rlkcdewsvn svgkiecvsa ettedciaki mngeadamsl dggfvyiagk
421  cglvpvlaen ynksdncedt peagyfavav vkksasdltw dnlkgkksch tavgrtagwn
481  ipmgllynki nhcrfdeffs egcapgskkd sslcklcmgs glnlcepnnk egyygytgaf
541  rclvekgdva fvkhqtvpqn tggknpdpwa knlnekdyel lcldgtrkpv eeyanchlar
601  apnhavvtrk dkeacvhkil rqqqhlfgsn vtdcsgnfcl frsetkdllf rddtvclakl
661  hdrntyekyl geeyvkavgn lrkcstssll eactfrrp
```

Figure 19 SEQ ID NO. 10 Human Albumin

```
  1 mkwvtfisll flfssaysrq vfrrdahkse vahrfkdlge enfkalvlia faqylqqcpf
 61 edhvklvnev tefaktcvad esaencdksl htlfgdklct vatlretyge madccakqep
121 ernecflqhk ddnpnlprlv rpevdvmcta fhdneetflk kylyeiarrh pyfyapellf
181 fakrykaaft eccqaadkaa cllpkldelr degkassakq rlkcaslqkf gerafkawav
241 arlsqrfpka efaevsklvt dltkvhtecc hgdllecadd radlakyice nqdsissklk
301 eccekpllek shciaevend empadlpsla adfveskdvc knyaeakdvf lgmflyeyar
361 rhpdysvvll lrlaktyett lekccaaadp hecyakvfde fkplveepqn likqncelfe
421 qlgeykfqna llvrytkkvp qvstptlvev srnlgkvgsk cckhpeakrm pcaedylsvv
481 lnqlcvlhek tpvsdrvtkc cteslvnrrp cfsalevdet yvpkefnaet ftfhadictl
541 sekerqikkq talvelvkhk pkatkeqlka vmddfaafve kcckaddket cfaeegkklv
601 aasqaalgl
```

Figure 20. SEQ ID NO. 11 Human Fc IgG1

```
  1 ggpsvflfpp kpkdtlmisr tpevtcvvvd vshedpevkf nwyvdgvevh naktkpreeq
 61 ydstyrvvsv ltvlhqdwln gkeykckvsn kalpapiekt iskakgqpre pqvytlppsr
121 eemtknqvsl tclvkgfyps diavewesng qpennykttp pvldsdgsff lyskltvdks
181 rwqqgnvfsc svmhealhnh ytqkslslsp gk
```

Figure 21. SEQ ID NO. 12 Human Fc IgG2

```
  1 astkgpsvfp lapcsrstse staalgclvk dyfpepvtvs wnsgaltsgv htfpavlqss
 61 glyslssvvt vtssnfgtqt ytcnvdhkps ntkvdktver kccvecppcp appvagpsvf
121 lfppkpkdtl misrtpevtc vvvdvshedp evqfnwyvdg mevhnaktkp reeqfnstfr
181 vvsvltvvhq dwlngkeykc kvsnkglpap iektisktkg qprepqvytl ppsreemtkn
241 qvsltclvkg fypsdiavew esngqpenny kttppmldsd gsfflysklt vdksrwqqgn
301 vfscsvmhea lhnhytqksl slspgk
```

Figure 22. SEQ ID NO. 13 Human Fc IgG3

```
  1 cytlllttp swvlsqvtlk esgpvlvkpt etltltctvs gfslsnakmg vswirqppgk
 61 alewlahifs ndeksystsl ksrltiskdt sksqvvltmt nmdpvdtaty ycariftity
121 snyvlqyyyy mdvwgkgttv tvssastkgp svfplapcsr stsgg
```

Figure 23. SEQ ID NO. 14 Human Fc IgG4

```
  1 apeflggpsv flfppkpkdt lmisrtpevt cvvvdvsqed pevqfnwyvd gvevhnaktk
 61 preeqfnsty rvvsvltvlh qdwlngkeyk ckvsnkglps siektiskak gqprepqvyt
121 lppsqeemtk nqvsltclvk gfypsdiave wesngqpenn ykttppvlds dgsfflyskl
181 tvdksrwqeg nvfscsvmhe alhnhytqks lslslgk
```

Figure 24. SEQ ID NO. 15 Human Fc Fragment Engineered For Extended Serum Half-Life

```
  1 ggpsvflfpp kpkdtlyitr epevtcvvvd vshedpevkf nwyvdgvevh naktkpreeq
 61 ynstyrvvsv ltvlhqdwln gkeykckvsn kalpapiekt iskakgqpre pqvytlppsr
121 deltknqvsl tclvkgfyps diavewesng qpennykttp pvldsdgsff lyskltvdks
181 rwqqgnvfsc svmhealhnh ytqkslsls
```

Figure 25. SEQ ID NO. 16 Human Fc Fragment Engineered For Lack Of Effector Functions

```
  1 thtcppcpap efeggpsvfl fppkpkdtlm isrtpevtcv vvdvshedpe vkfnwyvdgv
 61 evhnaktkpr eeqynstyrv vsvltvlhqd wlngkeykck vsnkalpasi ektiskakgq
121 prepqvytlp psreemtknq vsltclvkgf ypsdiavewe sngqpennyk ttppvldsdg
181 sfflyskltv dksrwqqgnv fscsvmheal hnhytqksls lspgk
```

Figure 26: SEQ ID NO. 17 p75NTR(NBP)-Fc linker (GGGGS)$n$ ($n = 1$ to $4$)

Figure 27: SEQ ID NO. 18 p75NTR(NBP)-Fc linker (EAAAK)$n$ ($n = 2$ to $5$)

Figure 28: SEQ ID NO. 19 p75NTR(NBP)-Fc linker

GGGGS

THERAPEUTIC USE OF P75NTR NEUROTROPHIN BINDING PROTEIN

CROSS REFERENCE TO RELATED APPLICATIONS

This application is a divisional of U.S. patent application Ser. No. 14/384,302, filed Sep. 10, 2014, which issued as U.S. Pat. No. 9,764,000, and which is a U.S. national stage filing under 35 U.S.C. § 371 of PCT International Application No. PCT/GB2013/050632, filed Mar. 14, 2013, which claims priority of U.S. Provisional Application No. 61/610,682 filed Mar. 14, 2012, the disclosures of which are incorporated by reference herein their entirety, including drawings.

BACKGROUND TO THE INVENTION

The neurotrophins, neurotrophic growth factor (NGF), brain-derived neurotrophic factor (BDNF), neurotrophin 3 (NT-3), and neurotrophin 4/5 (NT-4/5) act via four receptors: the low affinity p75 neutrophic receptor (p75NTR), and the high affinity tyrosine kinase receptors; TrkA, TrkB, and TrkC. The low affinity receptor p75NTR binds and is activated by all four neurotrophins and has been reported to function independently from the other receptors. However, the Trk receptors are more selectively activated i.e. NGF is the selective ligand for TrkA, BDNF the ligand for TrkB and NT-3, 4/5 the ligands for TrkC. In addition it has been reported, when p75NTR and Trk proteins are co-expressed, they form complexes, which alter the signaling of both receptors (Huang and Reichardt, 2003). Indeed, it has been suggested that p75NTR facilitates the selectivity of each of the neutrophins for their respective Trk receptor.

The p75NTR is a member of the tumor necrosis factor receptor superfamily (TNFR-SF) and was the first member of this superfamily to be characterized fully. The superfamily (encoded by some 30 genes in humans) is defined by ligand-binding domains consisting of one or more (typically four) repeats of a 40 amino acid cysteine-rich domain (CRD) that was first identified in p75NTR (Johnson et al., 1986; Radeke et al., 1987). In contrast, no sequence motif is shared by the intracellular domains of all TNFR-SF family members. Consequently, signaling mechanisms of TNFR-SF proteins vary significantly.

An unusual feature of p75NTR structure is the existence of a disulfide-linked p75NTR dimer, formed via cysteinyl residues within the transmembrane domains. This disulfide linkage is required for effective neurotrophin-dependent signaling by p75NTR and plays an important role in the formation of an intracellular and extracellular domain (Vilar et al., 2009b). Neurotrophins exist physiologically as non-covalently associated dimers (Bothwell and Shooter, 1977) with a distribution half-life of approximately 5 min (Tria et al., 1994). Neurotrophin-dependent p75NTR activation involves association of a neurotrophin dimer with CRDs 2-4 of the two extracellular domains of a p75NTR dimer (He and Garcia, 2004). Recent studies support a model in which neurotrophin binding causes the two extracellular domains of p75NTR dimers to move closer together, forcing the intracellular domains to splay apart in a snail-tong-like motion centered on the disulfide bond and permitting association of the intracellular domains with the signaling adapter proteins, NRIF and TRAF6 (Vilar et al., 2009a, 2009b). Intra-transmembrane domain disulfide bonds, such as are present in p75NTR, have not been described previously in other TNFR-SF family members, or in any other membrane protein.

p75NTR undergoes sequential proteolytic cleavage by α-secretase and γ-secretase activities and matrix metalloproteinases (MMPs), releasing its intracellular domain (ICD) into the cytoplasm, in a manner analogous to the cleavage-dependent signaling pathway of Notch and β-amyloid precursor protein (Jung et al., 2003; Kanning et al., 2003). Cytoplasmic release of the p75NTR ICD by this pathway promotes signaling by associated NRIF (Kenchappa et al., 2006). The role of the extracellular domain of p75NTR, following the proteolytic cleavage by α-secretase and γ-secretase activities and MMPs isn't fully understood.

It has been documented that NGF and other neurotrophins (BDNF, NT-3 and NT-4/5) play a significant role in pathology for example pain due to osteoarthritis, pancreatitis, rheumatoid arthritis, psoriasis, pruritis and multiple sclerosis (Watanabe et al., 2010; Raychaudhuri et al., 2011; Barthel et al., 2009; Truzzi et al., 2011; McDonald et al., 2011; Yamaoka et al., 2007). It was been demonstrated that selective antibodies to any of the neutrophins; either NGF or BDNF, NT-3 and NT-4/5 significantly reduce pain. Furthermore, antibodies directed to the neurotrophin receptors p75NTR Trk A, Trk B or Trk C have also been demonstrated to be efficacious in models of pain (Orita S et al., 2010; Svensson P et al., 2010; Iwakura et al., 2010; Cirilio et al., 2010; Pezet et al., 2010; Hayashi et al., 2011; Chu et al., 2011; Ueda et al., 2010; Ghilardi et al., 2010; Fukui et al., 2010). Fukui et al., (2010) in a model of pain (mechanical allodynia following sciatic nerve crush) demonstrated significant efficacy on pain related endpoints following treatment with an anti-p75NTR antibody. It was concluded from this study that the treatment with a p75NTR inhibitory antibody reduced CGRP and p75NTR expression resulting in a significant reduction in pain.

The current invention demonstrates the extracellular domain of p75NTR, exogenous or endogenous following cleavage from the cell membrane, acts as a neurotrophin binding protein or soluble receptor to each of the neurotrophins NGF, BDNF, NT-3 and NT-4/5 and plays a significant role in the function, physiology and homeostasis of neurotrophin function. Moreover, we describe the use of the extracellular domain of p75NTR for modulating or neutralizing the pathological actions of the neurotrophic factors including NGF, BDNF, NT-3 and NT4/5, for example in models of static allodynia and thermal hyperalgesia. Thus the p75NTR neurotrophin binding protein finds use in the treatment of pain and other neurotrophic factor related pathologies such as psoriasis, eczema, rheumatoid arthritis, cystitis, endometriosis and osteoarthritis.

BRIEF DESCRIPTION OF THE INVENTION

According to a first aspect of the present invention there is provided a p75NTR neurotrophin binding protein, (NBP), for use in the treatment of pain, or for the prevention and/or treatment of pain and/or symptoms of pain or for ameliorating, controlling, reducing incidence of, or delaying the development or progression of pain and/or symptoms of pain. According to a second aspect of the present invention there is provided a p75NTR neurotrophin binding protein for use according to the first aspect wherein, the p75NTR(NBP) comprises p75NTR(NBP) connected to one or more auxiliary molecules. Preferably, the p75NTR(NBP) is connected to the one or more auxiliary molecules via one or more linkers. According to a third aspect of the invention there is provided a nucleic acid molecule encoding the p75NTR (NBP) or p75NTR(NBP) connected to one or more auxiliary molecules of the p75NTR(NBP) according to the first or second aspects the nucleic acid molecule may further comprise encoding a signal sequence. Also provided is the use of the nucleic acid molecule for the treatment of pain. According to a fourth aspect of the invention there is provided a replicable expression vector for transfecting a cell, the vector comprising the nucleic acid molecule of the third aspect, preferably the vector is a viral vector. Also provided is the use of the vector for the treatment of pain. According to a fifth aspect of the invention there is provided a host cell harbouring the nucleic acid molecule of either the third or fourth aspect. According to a sixth aspect of the invention there is provided the p75NTR(NBP) for use according to the first or second aspect or the preferred embodiments thereof, or the nucleic acid or vector for use according to the third and fourth aspects wherein the p75NTR(NBP) or the nucleic acid molecule or vector is for separate, sequential or simultaneous use in a combination combined with a second pharmacologically active compound.

DESCRIPTION OF THE FIGURES

FIG. 1. p75NTR extracellular domain sequence, neurotrophin binding domains highlighted in bold (SEQ ID NO:1).

FIG. 2 [a] and FIG. 2 [b]. p75NBPP peptide standard fragments and co-immunoprecipitation of p75NTR(NBP) and NGF demonstrating p75NTR(NBP)-NGF complex in human plasma, where the peaks at 11.0, 13.74, and 15.2 mins refer to SEQ ID NOs:4, 7, and 6, respectively. FIG. 2 [a] shows detection of p75NTR extracellular domain standard. FIG. 2 [b] shows detection of p75 extracellular domain from total NGF assay using commercial human serum.

FIG. 3. MS/MS sequence confirmation of the WADAE-CEEIPGR (SEQ ID NO. 7) peak shown in FIGS. 2a and 2b.

FIG. 4. p75NTR(NBP) inhibits NGF function in U2OS cell line expressing TrkA (top panel) and in U20S cell line co-expressing TrkA and p75NTR (bottom panel).

FIG. 5. Soluble p75NTR(NBP) inhibits BDNF function in U2OS cell line expressing TrkA (top panel) and in U2OS cell line co-expressing TrkA and p75NTR (bottom panel).

FIG. 6. Biocore data demonstrating p75NTR(NBP) binding to BDNF and competition between anti-BDNF and p75NTR(NBP).

FIG. 7. p75NTR(NBP) inhibition of NGF activity in PC12 cells. Top shows significant inhibition of activity in cultured cells. Bottom shows change in cell number for different concentrations of p75NTR(NBP).

FIG. 8. Neurotrophin Binding Protein p75NTR(NBP) inhibits BDNF pain effect in a model of nerve excitability. Top half of figure shows before (upper) and 45 minutes after (lower) administration of BDNF, demonstrating a significant increase in neuronal excitability. Bottom half of figure demonstrates that the addition of p75NTR(NBP) to the media significantly reduced the neuronal excitability in response to pinching stimuli.

FIG. 9. Neurotrophin Binding Protein p75NTR(NBP) inhibits hyperalgesia in UVIH model FIG. 10. SEQ ID NO. 1 Human p75NTR full amino acid sequence FIG. 11. SEQ ID NO. 2 Human p75NTR extracellular domain including signal sequence FIG. 12. SEQ ID NO. 3 Human p75NTR extracellular domain without signal sequence FIG. 13. SEQ ID NO. 4 Human p75NTR(NBP) neurotrophin binding domain 1

FIG. 14. SEQ ID NO. 5 Human p75NTR(NBP) neurotrophin binding domain 2

FIG. 15. SEQ ID NO. 6 Human p75NTR(NBP) neurotrophin binding domain 3

FIG. 16. SEQ ID NO. 7 Human p75NTR(NBP) neurotrophin binding domain 4

FIG. 17. SEQ ID NO. 8 Human p75NTR(NBP) neurotrophin binding domain 5

FIG. 18. SEQ ID NO. 9 Human Transferrin

FIG. 19. SEQ ID NO. 10 Human Albumin

FIG. 20. SEQ ID NO. 11 Human Fc IgG1

FIG. 21. SEQ ID NO. 12 Human Fc IgG2

FIG. 22. SEQ ID NO. 13 Human Fc IgG3

FIG. 23. SEQ ID NO. 14 Human Fc IgG4

FIG. 24. SEQ ID NO. 15 Human Pc Fragment Engineered For Extended Serum Half-Life FIG. 25. SEQ ID NO. 16 Human Fc Fragment Engineered For Lack Of Effector Functions FIG. 26. SEQ ID NO 17 p75NTR(NBP)-Fc linker FIG. 27: SEQ ID NO. 18 p75NTR(NBP)-Fc linker FIG. 28: SEQ ID NO. 19 p75NTR(NBP)-Fc linker

DETAILED DESCRIPTION OF THE INVENTION

According to a first aspect of the present invention there is provided a p75NTR neurotrophin binding protein, (p75NTR(NBP)), for use in the treatment of pain, or for the prevention and/or treatment of pain and/or symptoms of pain or for ameliorating, controlling, reducing incidence of, or delaying the development or progression of pain and/or symptoms of pain. Preferably the p75NTR neurotrophin binding protein, p75NTR(NBP), is pegylated, further preferably it is glycosylated.

The p75NTR neurotrophin binding protein, p75NTR (NBP), preferably comprises (a) one or more of neurotrophin binding domain 1 [SEQ ID NO. 4], 2 [SEQ ID NO. 5], 3 [SEQ ID NO. 6], 4 [SEQ ID NO. 7] or 5 [SEQ ID NO. 8]. Further preferably the p75NTR(NBP) comprises (b) each of neurotrophin binding domain 1 [SEQ ID NO. 4], 2 [SEQ ID NO. 5], 4 [SEQ ID NO. 7] and 5 [SEQ ID NO. 8] or (c) each of neurotrophin binding domain 1 [SEQ ID NO. 4], 3 [SEQ ID NO. 6], 4 [SEQ ID NO. 7] and 5 [SEQ ID NO. 8]. Further preferably the p75NTR(NBP) comprises extracellular domain 2 [SEQ ID NO. 3] or a portion thereof comprising (a), (b) or (c) above. Further preferably the p75NTR(NBP) comprises extracellular domain 1 [SEQ ID NO. 2] or a portion thereof comprising (a), (b) or (c) above.

Preferably the p75NTR(NBP) binds to each of the neurotrophins NGF, NT3, BDNF and NT4/5, preferably human NGF, NT3, BDNF and NT4/5. Further preferably the p75NTR(NBP) binds to each of the neurotrophins NGF, NT3, BDNF and NT4/5, preferably human NGF, NT3, BDNF and NT4/5, preferably with a binding constant equivalent to or the same as the native complete sequence p75NTR [SEQ ID NO. 1]. Binding constants can be determined using the assays described herein such as by use of surface plasmon resonance at 20° C., assays for the native protein binding constants are known and comprise cell based assays known in the art. Preferably the p75NTR(NBP) protects one or more of the aforementioned neurotrophins from degradation in plasma or other bodily fluids, in-vitro or in-vivo, and/or maintain a homeostatic balance of one or more of the aforementioned neurotrophins compared to their biologically free form.

The p75NTR(NBP) of the present invention preferably binds to any one or more of NGF, BDNF, NT3 or NT4/5 with a binding affinity ($K_d$) of between about 0.1 nM to about 50 nM. In some preferred embodiments, the binding affinity ($K_d$) is between about 0.1 nM and any of about 0.2 nM, 0.5 nM, 1 nM, 1.5 nM, 2 nM, 2.5 nM, 3 nM, 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM, 15 nM, 20 nM, 25 nM, 30 nM, 35 nM, 40 nM, 45 nM or 50 nM as measured in an in vitro binding assay for NGF, BDNF, NT3 or NT4/5 such as described herein preferably as measured by surface plasmon resonance at 20° C. In some further preferred embodiments, binding affinity ($K_d$) is or is less than any of about 250 pM, 300 pM, 350 pM, 400 pM, 450 pM, 500 pM, 550 pM, 600 pM, 650 pM, 700 pM, 750 pM, 800 pM, 850 pM, 950 pM or 1 nM as measured in an in vitro binding assay for p75NTR(NBP) with the neurotrophins such as described herein, preferably as measured by surface plasmon resonance at 20° C. In a further more preferred embodiment the binding affinity ($K_d$) is about 0.3 nM or about 1 nM, as measured in an in vitro binding assay for p75NTR(NBP) with the neurotrophins such as described herein, preferably as measured by surface plasmon resonance at 20° C.

Further preferably the p75NTR(NBP) effects the functional activity of the aforementioned neurotrophins, (defined as modulating or up or down regulating the functional activity of the neurotrophins) NGF, BDNF, NT3 or NT4/5, for example the functional activity of the aforementioned neurotrophins resulting from their interaction with their respective receptors.

Preferably the p75NTR(NBP) effects the functional activity of BDNF as assessed by functional assay of any of growth and differentiation of neurons and synapses, survival and differentiation in neuronal cell culture, Trk signalling, stimulation of axon outgrowth in vitro or in vivo.

Preferably the p75NTR(NBP) effects the functional activity of NGF as assessed by measuring NGF binding to and activation of TrkA, as demonstrated in classical neuron survival assays (such as provided in Cowan, W. M., Hamburger, V., Levi-Montalcini, R. *Annu. Rev. Neurosci.* 2001; 24:551-600).

Preferably the p75NTR(NBP) effects the functional activity of NT3 as assessed by measuring NT3 binding to and activation of endogenous Trk receptor activity, as demonstrated in Trk receptor phosphorylation, mitogen-activated protein kinase phosphorylation reporter assays or cell survival and neurite extension assays.

Preferably the p75NTR(NBP) effects the functional activity of NT4/5 as assessed by measuring NT4/5 in vitro or in vivo phosphorylation and activation assays for example in myelin basic protein (MBP) phosphorylation assays or alternatively in vivo in a Matrigel angiogenesis assay of vascular endothelial growth factor (VEGF)/basic fibroblast growth factor-induced angiogenesis.

Preferably the p75NTR(NBP) binds to the contact residues of one or more of the neurotrophins NGF, NT3, BDNF and NT4/5 as shown in He and Garcia (2001) Science, 301, pages 870-805.

Preferably the p75NTR(NBP) is soluble, preferably soluble in aqueous solution, preferably soluble in a biological fluid such as serum, plasma, blood.

According to a second aspect of the present invention there is provided a p75NTR(NBP) for use according to the first aspect wherein, the p75NTR(NBP) comprises p75NTR (NBP), preferably the p75NTR(NBP) of the first aspect, connected to one or more auxiliary molecules. Preferably, the p75NTR(NBP) is connected to the one or more auxiliary molecules via one or more linkers.

Preferably the one or more auxiliary molecules are selected from; (a) transferrin or a portion thereof, preferably the transferrin is human transferrin, preferably SEQ ID NO. 9, (b) albumin or a portion thereof, preferably the albumin is human albumin, preferably SEQ ID NO. 10 (c) an immunoglobulin Fc or a portion thereof, preferably the immunoglobulin Fc is human immunoglobulin Fc, (d) a polyethylene glycol polymer chain (e) a carbohydrate chain.

As used herein, the term, "immunoglobulin Fc" or "Ig Fc" is understood to mean the carboxyl-terminal portion of an immunoglobulin chain constant region, preferably an immunoglobulin heavy chain constant region, or a portion thereof. Preferably the immunoglobulin Fc comprises 1) a CH1 domain, a CH2 domain, and a CH3 domain, optionally with an immunoglobulin hinge region, 2) a CH1 domain and a CH2 domain, optionally with an immunoglobulin hinge region, 3) a CH1 domain and a CH3 domain, optionally with an immunoglobulin hinge region, 4) a CH2 domain and a CH3 domain, optionally with an immunoglobulin hinge region or 5) a combination of two or more domains selected from CH1, CH2 and CH3 optionally combined with an immunoglobulin hinge region. Preferably the immunoglobulin Fc comprises at least an immunoglobulin hinge region, a CH2 domain and a CH3 domain, and optionally a CH1 domain. Preferably the immunoglobulin Fc comprises or consists of an Fc or a portion of an Fc of an immunoglobulin of isotype selected from IgG, IgM, IgA, IgD, IgE, further preferably, IgG1, IgG2, IgG3, IgG4, IgA1, IgA2, sIgA, more preferably IgG2 or IgG4, most preferably IgG2. Optionally the immunoglobulin Fc also comprises amino acid mutations, deletions, substitutions or chemical modifications which serve to minimise complement fixation or antibody-dependent cellular cytotoxicity or which improve affinity of binding to the Fc receptor.

Further preferably the immunoglobulin Fc comprises or consists of any of: (a) a CH2 domain or portion thereof and a CH3 domain or portion thereof, (b) a CH2 domain or portion thereof, or (c) a CH3 domain or portion thereof, wherein the immunoglobulin Fc or portion thereof is of isotype selected from IgG, IgM, IgA, IgD, IgE, further preferably, IgG1, IgG2, IgG3, IgG4, IgA1, IgA2, sIgA, more preferably IgG2 or IgG4, most preferably IgG2.

Preferably the immunoglobulin Fc comprises or consists of the carboxy terminal region of an immunoglobulin heavy chain and may comprise the CH2 and/or CH3 domains, or parts thereof, from IgG, IgA or IgD antibody isotypes, or the CH2 and/or CH3 and/or CH4 domains, or parts thereof from IgM or IgE. Preferably the immunoglobulin Fc comprises or consists of a fragment of the Fc, comprising mainly CH3 and a small portion of CH2, as is derivable by pepsin digestion of the immunoglobulin. Preferably the immunoglobulin Fc comprises or consists of the full Fc region, comprising CH2 and CH3, additionally connected to the hinge region which is a short segment of heavy chain connecting the CH1 and CH2 regions in the intact immunoglobulin, as may be produced by papain digestion of the immunoglobulin. Preferably the immunoglobulin hinge region comprises or consists of a hinge region or part of a hinge region derived from an IgG preferably human IgG, more preferably selected from IgG1, IgG2, IgG3, or IgG4, most preferably IgG1 or is alternatively a species or allelic variant of the foregoing hinge region embodiments. The hinge region or a part of an immunoglobulin hinge region can be located at the C or N-terminal end of the Fc region, preferably at the N-terminal end.

According to a preferred embodiment of the present invention the immunoglobulin Fc preferably comprises or consists of an Fc or a portion of an Fc of an immunoglobulin which comprises one or more amino acid mutations of the wild type sequence in the CH2 region which reduce Fc effector function. Preferably these mutations are A330, P331 to 5330, 5331 (amino acid numbering with reference to the wildtype IgG2 sequence, wherein the CH2 region is in the human heavy chain IgG2 constant region: [Eur. J. Immunol. (1999) 29:2613-2624]. Preferably the immunoglobulin Fc is glycosylated and highly charged at physiological pH hence helping solubilise the p75NTR(NBP). The Fc region also permits detection of the p75NTR(NBP) by anti-Fc ELISA for example in diagnostic purposes. The p75NTR(NBP) of the invention is preferably synthesized in a cell which glycosylates the Ig Fc preferably at normal glycosylation sites.

Preferably the immunoglobulin Fc comprises or consists of a human immunoglobulin Fc region of amino acid sequence selected from SEQ ID No. 11, 12, 13, 14, 15 or 16 or a species or allelic variant thereof, or the CH2 and or CH3 domains, or portions thereof derived from SEQ ID NO. 11, 12, 13, 14, 15 or 16.

According to the present invention, the p75NTR(NBP) connected to one or more auxiliary molecules preferably demonstrates advantageous biological properties of improved solubility of p75NTR(NBP) and/or stability of p75NTR(NBP) and/or improved serum half life p75NTR(NBP). Improved solubility is desirable in order that bioavailability of the p75NTR(NBP) is maximized on administration and accurate dosage of the p75NTR(NBP) can be determined and carried out. Improved solubility is advantageous to overcome the problem of aggregates which are undesirable causing pain in delivery in-vivo and leading to potential inflammation. Improved serum half life has the advantage of facilitating reduced levels or reduced frequency of dose requirement during use for treatment in order to achieve the equivalent or maintained therapeutic effect of the p75NTR(NBP) delivered. A prolonged half life and higher stability in blood or serum has the advantage of permitting a dosage regime of less frequent dosing and/or lower dosing levels hence reducing potential toxicity or side effects in-vivo. In this case the p75NTR(NBP) is more potent in its therapeutic effect and/or more stable in the circulation. The resulting lower or less frequent doses are advantageous in minimising any potential toxic effects or side effects potentially associated with p75NTR(NBP) administration. The molecular weight of the p75NTR(NBP) connected to one or more auxiliary molecules is also increased over p75NTR(NBP) alone, this has the advantage that the molecule will be well retained in the blood circulation when administered intravenously reducing the risk of penetration to undesired sites for example the central nervous system and making the molecule suitable for retention or concentration in the tissues targeted.

Preferably the p75NTR(NBP) connected to one or more auxiliary molecules demonstrates improved solubility of p75NTR(NBP) and/or improved stability of p75NTR(NBP) and/or improved serum half life in comparison to p75NTR(NBP) not so connected. Preferably the improved solubility is solubility in an aqueous solution such as water preferably with excipients such as buffers and/or salts at preferably at a physiological pH, preferably at between pH 5 to pH 8, preferably about pH 7, or is solubility in a biological fluid such as serum or blood. Preferably the improved stability is stability of activity or structural integrity of the p75NTR(NBP) protein due to the effects of denaturation, oxidation, fragmentation or aggregation over a period of time, during a period storage or following freeze and thaw. Structural stability can be judged by standard measures of denaturation, oxidation, aggregation or aggregation, stability of activity can be measured by the binding or functional assays disclosed herein, methods of measuring protein serum half life are known.

Preferably the p75NTR(NBP) connected to one or more auxiliary molecules can be expressed at high levels from variety of mammalian host cells to provide a single species and can be efficiently purified by affinity chromatography for example by binding to *Staphylococcus aureus* protein A. Preferably the p75NTR(NBP) connected to one or more auxiliary molecules can dimerise and preferably the dimer has increased affinity to neurotrophins NGF, BDNF, NT3 or NT4/5 in comparison to p75NTR(NBP) not so connected. Tighter binding has the advantage of higher potency and a higher therapeutic efficacy as judged by the p75NTR(NBP) effects for example as determined by neurotrophin functional assays disclosed herein. Higher potency has the benefit that the p75NTR(NBP) can be used at lower dosage amounts to achieve the same therapeutic efficacy hence reducing potential toxicity or side effects in-vivo.

Preferably the p75NTR(NBP) of the invention has a half life in-vivo of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 hours+/−1 hour, further preferably the p75NTR(NBP) of the invention has a half life in-vivo of about or more than 24 hours.

Further preferably the p75NTR(NBP) of the invention has a half life in-vitro of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 days+/−1 day, further preferably the p75NTR(NBP) of the invention has a half life in-vitro of about or more than 6 days. Preferably the stability is measured at about physiological pH, in a buffered aqueous solution, preferably at 20° C. or 37° C.

According to the foregoing preferred embodiments, preferably the in-vivo half life is half life in rat or half life in human, more preferably in human. Preferably the half life is determined from serum measurements of the levels of p75NTR(NBP) of the invention following administration in-vivo for example by intravenous or subcutaneous injection.

Further according to the second aspect of the invention the linker is preferably selected from: (a) a covalent bond, (b) non covalent bond, (c) a peptide bond, (d) one amino acid or a plurality of amino acids comprising a peptide. Preferably the p75NTR(NBP) is connected to more than one auxiliary molecule, optionally each auxiliary molecule is either the same or different or a mixture of the same and different. Further preferably the more than one auxiliary molecule comprises a multimer or a plurality of auxiliary molecules linked to p75NTR(NBP) via a linker, and wherein each molecule may be there same or different or a mixture of the same and different.

Preferably the linker comprises or consists of one or a plurality of amino acids or comprises or consists of a polypeptide sequence of amino acids, preferably about 1 to about 25 amino acids, preferably any one of 1, 2, 3, 4, 5, 6, 7, 8, or 9 amino acids further preferably any one of about 10, 11, 12, 13, 14, 15, 16, 17, 18, 19, 20, 21 22, 23 or 24 amino acids, most preferably 13 amino acids.

Preferably the linker comprises or consists of a polypeptide sequence of amino acids that lacks any stable secondary structure such as alpha helix, beta strand, 310 helix and pi helix, polyproline helix, alpha sheet. Preferably the linker region comprises or consists of a polypeptide sequence of amino acids that defines a flexible or dynamic or unstructured polypeptide such as for example a flexible loop, random coil or flexible turn, such unstructured polypeptides are often found connecting regions of secondary structure in large protein molecules.

Preferably the linker is a polypeptide sequence of amino acids that comprises greater than or about 50% glycine and/or alanine and/or serine in p75NTR(NBP), further preferably greater than or about 55%, 60%, 65%, 70%, 75%, 80%, 85%, 90%, 95% or 100% glycine and/or alanine and/or serine in p75NTR(NBP). Preferably the linker region comprises or consists of a polypeptide sequence of amino acids that comprises both glycine and serine, preferably with a greater proportion of glycine that serine, preferably the linker region comprises or consists of flexible linkers, SEQ ID NO. 17 (GGGGS)n (n=1 to 4), or helical linkers, SEQ ID NO. 18 (EAAAK)n (n=2 to 5) or polypeptide linkers predominantly including amino acid residues selected from glycine, serine, alanine, and threonine ranging from 1 to 10 repeats of each amino acid and any combination thereof.

Preferably the linker overcomes or prevents steric hindrance from the auxiliary molecule which could interfere with the aforementioned neurotrophin binding ability or biological activity of the p75NTR(NBP) when compared to p75NTR(NBP) which is not linked to an auxiliary molecule. Hence the linker region preferably permits flexibility between the p75NTR(NBP) and the auxiliary molecule and allows retention of or improvement of the aforementioned biological activity of p75NTR(NBP) in comparison to free or native p75NTR(NBP) not so linked as determined by binding to neurotrophins using binding assays such as described herein.

Further preferably the linker is immunologically inert, such that it does not trigger complement mediated lysis, does not stimulate antibody-dependent cell mediated cytotoxicity (ADCC), does not activate microglia or T-cells. Preferably the linker region is reduced in one or more of these activities.

Further preferably the linker comprises or consists of a polypeptide known or predicted from structural analysis or structural prediction to be a flexible or dynamic or unstructured polypeptide or to lack a stable secondary structure.

Most preferably the linker comprises or consists of a polypeptide of sequence of SEQ ID NO. 19 (GGGGS).

The p75NTR(NBP) of the invention may also comprise a proteolytic cleavage site, optionally interposed between the p75NTR(NBP) and the auxiliary molecule. The proteolytic cleavage site may be located in the linker or at the junction of the linker with either the p75NTR(NBP) or/and the auxiliary molecule. The p75NTR(NBP) may optionally be cleaved from the auxiliary molecule prior to formulation and or administration for therapeutic purposes.

Preferably the linker and/or the one or more auxiliary molecules do not impair or significantly impair the p75NTR (NBP):

(a) effect on the functional activity of the neurotrophins (defined as modulating or up or down regulating the functional activity of the neurotrophins) NGF, BDNF, NT3 or NT4/5, (b) binding affinity for any of NGF, BDNF, NT3 or NT4/5 with a binding affinity of between about 0.1 nM to about 50 nM (c) ability to binds to each of the neurotrophins NGF, NT3, BDNF and NT4/5, preferably human NGF, NT3, BDNF and NT4/5.

According to a preferred embodiment of aspects one and two of the present invention there is provided a p75NTR (NBP) of the present invention there is provided a p75NTR (NBP) for use in treating pain wherein the p75NTR(NBP) consists of: (A) a P75NTR(NBP) of sequence SEQ ID NO. 3, and optionally (B) an immunoglobulin Fc, and further optionally consisting of sequence SEQ ID NO. 11 and optionally (C) a linker, optionally consisting of SEQ ID NO. 19.

According to a third aspect of the invention there is provided a nucleic acid molecule encoding the p75NTR (NBP) or p75NTR(NBP) connected to one or more auxiliary molecules according to the first or second aspects. Preferably the nucleic acid molecule is for use in the treatment of pain.

According to a preferred embodiment of the present invention the nucleic acid molecule may further comprise a region encoding a signal sequence, preferably a p75NTR signal sequence for example a DNA or RNA sequence.

According to a fourth aspect of the invention there is provided a replicable expression vector for transfecting a cell, the vector comprising the nucleic acid molecule of the third aspect, preferably the vector is a viral vector. Preferably the vector is for use in the treatment of pain.

Further according to the third or fourth aspects of the invention there is provided a method of expressing the nucleic acid molecule or the vector of the invention to produce or secrete the p75NTR(NBP) or p75NTR(NBP) connected to one or more auxiliary molecules. Preferably the method comprises the introduction of the nucleic acid molecule or vector into a cell and expression of the nucleic acid therein to produce or secrete the p75NTR(NBP) or p75NTR (NBP) connected to one or more auxiliary molecules. Preferably the nucleic acid molecule or vector is introduced into the cell in-vitro alternatively in-vivo. Preferably the expressed p75NTR(NBP) or p75NTR(NBP) connected to one or more auxiliary molecules is expressed in-vitro, optionally further isolated and purified, alternatively preferably the expressed p75NTR(NBP) or p75NTR(NBP) connected to one or more auxiliary molecules is expressed in-vivo, preferably the in-vivo expression constitutes gene therapy. Preferably the vector is a replicable expression vector, optionally for transfecting a mammalian cell, preferably the vector is a viral vector.

According to a fifth aspect of the invention there is provided a host cell harbouring the nucleic acid molecule or vector of either the third or fourth aspect, preferably the cell is a mammalian cell.

According to a sixth aspect of the invention there is provided the p75NTR(NBP) for use according to the first or second aspect or the preferred embodiments thereof, or the nucleic acid or vector for use according to the third and fourth aspects wherein, the pain or symptom of pain is selected from:

(a) acute pain and/or spontaneous pain, (b) chronic pain and or on-going pain, (c) inflammatory pain including any one of arthritic pain, pain resulting from osteoarthritis or rheumatoid arthritis, resulting from inflammatory bowel diseases, psoriasis and eczema (d) nociceptive pain, (e) neuropathic pain, including painful diabetic neuropathy or pain associated with post-herpetic neuralgia, (f) hyperalgesia, (g) allodynia, (h) central pain, central post-stroke pain, pain resulting from multiple sclerosis, pain resulting from spinal cord injury, or pain resulting from Parkinson's disease or epilepsy, (i) cancer pain, (j) post-operative pain, (k) visceral pain, including digestive visceral pain and non-digestive visceral pain, pain due to gastrointestinal (GI) disorders, pain resulting from functional bowel disorders (FBD), pain resulting from inflammatory bowel diseases (IBD), pain resulting from dysmenorrhea, pelvic pain, cystitis, interstitial cystitis or pancreatitis, (l) musculo-skeletal pain, myalgia, fibromyalgia, spondylitis, sero-negative (non-rheumatoid) arthropathies, non-articular rheumatism, dystrophinopathy, Glycogenolysis, polymyositis, pyomyositis, (m) heart or vascular pain, pain due to angina, myocardical infarction, mitral stenosis, pericarditis, Raynaud's phenomenon, scleredoma, scleredoma or skeletal muscle ischemia, (n) head pain including migraine, migraine with aura, migraine without aura cluster headache, tension-type headache.

(o) orofacial pain, including dental pain, temporomandibular myofascial pain or tinnitus, or (p) back pain, bursitis, menstrual pain, migraine, referred pain, trigeminal neuralgia, hypersensitisation, pain resulting from spinal trauma and/or degeneration or stroke.

According to a seventh aspect of the invention there is provided the p75NTR(NBP) for use according to the first or second aspect or the preferred embodiments thereof, or the nucleic acid molecule or vector for use according to the third and fourth aspects wherein the p75NTR(NBP) or the nucleic acid molecule or vector is for separate, sequential or simultaneous use in a combination combined with a second pharmacologically active compound. Preferably the second pharmacologically active compound of the combination is selected from;

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorocyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

- a 5-HT receptor agonist or antagonist, particularly a 5-HT$_{1B/1D}$ agonist such as eletriptan, sumatriptan, naratriptan, zolmitriptan or rizatriptan;
- a 5-HT$_{2A}$ receptor antagonist such as R(+)-alpha-(2,3-dimethoxy-phenyl)-1-[2-(4-fluorophenylethyl)]-4-piperidinemethanol (MDL-100907);
- a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
- Tramadol®;
- a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-c]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;
- a cannabinoid;
- metabotropic glutamate subtype 1 receptor (mGluR1) antagonist;
- a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
- a noradrenaline (norepinephrine) reuptake inhibitor, such as maprotiline, lofepramine, mirtazepine, oxaprotiline, fezolamine, tomoxetine, mianserin, buproprion, buprorpion metabolite hydroxybuproprion, nomifensine and viloxazine (Vivalan®), especially a selective noradrenaline reuptake inhibitor such as reboxetine, in particular (S,S)-reboxetine;
- a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;
- an inducible nitric oxide synthase (iNOS) inhibitor such as S-[2-[(1-iminoethyl)amino]ethyl]-L-homocysteine, 5-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;
- an acetylcholinesterase inhibitor such as donepezil;
- a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;
- a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,
- a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504);
- a sodium channel blocker, such as lidocaine; or
- a 5-HT3 antagonist, such as ondansetron;

and the pharmaceutically acceptable salts and solvates thereof.

According to an eighth aspect of the present invention there is provided a method of treating, preventing, ameliorating, controlling, reducing incidence of, or delaying the development or progression of pain or any of the foregoing pain and/or symptoms of pain in an individual, comprising administration to the individual of an effective amount of the p75NTR(NBP) according to the first, second or seventh aspect or the preferred embodiments thereof, or the nucleic acid molecule or vector according to the third and fourth aspects.

Preferably the individual is a mammal, for example a companion animal such as a horse, cat or dog or a farm animal such as a sheep, cow or pig. Most preferably the mammal is a human.

According to a ninth aspect of the present invention there is provided a pharmaceutical composition for any one or more of treating, preventing, ameliorating, controlling, reducing incidence of, or delaying the development or progression of pain or any of the foregoing pain/or symptoms, comprising the p75NTR(NBP) according to the first, second or seventh aspect or the preferred embodiments thereof, or the nucleic acid molecule or vector according to the third and fourth aspects and a pharmaceutically acceptable carrier and/or an excipient.

Preferably the p75NTR(NBP) according to the first, second or seventh aspects or the preferred embodiments thereof, or the nucleic acid molecule or vector according to the third and fourth aspects or the pharmaceutical composition of the ninth aspect is prepared for or suitable for oral, sublingual, buccal, topical, rectal, inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local or epicutaneous administration.

Preferably the p75NTR(NBP) according to the first, second or seventh aspect or the preferred embodiments thereof, or the nucleic acid molecule or vector according to the third and fourth aspects or the pharmaceutical composition of the ninth aspect is prepared for or suitable for administration prior to and/or during and/or after the onset of pain or for such use.

Preferably the p75NTR(NBP) according to the first, second or seventh aspect or the preferred embodiments thereof, or the nucleic acid molecule or vector according to the third and fourth aspects or the pharmaceutical composition of the ninth aspect is for or prepared for administration between once to 7 times per week, further preferably between once to four times per month, further preferably between once to six times per 6 month period, further preferably once to twelve times per year. Preferably the medicament is to be or prepared to be peripherally administered in a period selected from: once daily, once every two, three, four, five or six days, weekly, once every two weeks, once every three weeks, monthly, once every two months, once every three months, once every four months, once every five months, once every six months, once every seven months, once every eight months, once every nine months, once every ten months, once every eleven months or yearly.

Further preferably the p75NTR(NBP) according to the first, second or seventh aspect or the preferred embodiments thereof, or the nucleic acid molecule or vector according to the third and fourth aspects or the pharmaceutical composition of the ninth aspect is to be or prepared to be peripherally administered via a route selected from one or more of; orally, sublingually, buccally, topically, rectally, via inhalation, transdermally, subcutaneously, intravenously, intra-arterially or intramuscularly, via intracardiac administration, intraosseously, intradermally, intraperitoneally, transmucosally, vaginally, intravitreally, epicutaneously, intra-articularly, peri-articularly or locally.

Preferably the p75NTR(NBP) according to the first, second or seventh aspect or the preferred embodiments thereof, or the nucleic acid molecule or vector according to the third and fourth aspects or the pharmaceutical composition of the ninth aspect is for or is prepared for administration at a concentration of between about 0.1 to about 200 mg/ml; preferably at any one of about 0.5, 1, 5, 10, 15, 20, 25, 30, 35, 40, 45, 50, 55, 60, 65, 70, 75, 80, 85, 90, 95, 100, 110, 120, 130, 140, 150, 160, 170, 180, 190 or 200 mg/ml+/− about 10% error, most preferably at about 50 mg/ml.

Preferably the p75NTR(NBP) according to the first, second or seventh aspect or the preferred embodiments thereof, or the nucleic acid molecule or vector according to the third and fourth aspects or the pharmaceutical composition of the ninth aspect is for or is prepared for administration at a concentration of between about 0.1 to about 200 mg/kg of body weight; preferably at any one of about 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190 or about 200 mg/kg of body weight+/−about 10% error, most preferably at about 10 mg/kg.

According to a tenth aspect of the present invention there is provided a kit comprising:

(a) the p75NTR(NBP) according to the first, second or seventh aspect or the preferred embodiments thereof, or the nucleic acid molecule or vector according to the third and fourth aspects or the pharmaceutical composition of the ninth aspect; and (b) instructions for the administration of an effective amount of said p75NTR(NBP), nucleic acid molecule, vector or pharmaceutical composition to an individual for any one or more of the prevention or treatment of pain and/or symptoms of pain or for ameliorating, controlling, reducing incidence of, or delaying the development or progression of pain and/or symptoms of pain.

The kit may include one or more containers containing the p75NTR(NBP), nucleic acid, vector or pharmaceutical composition described herein and instructions for use in accordance with any of the methods and uses of the invention. The kit may further comprise a description of selecting an individual suitable for treatment based on identifying whether that individual has a pain or a symptom of pain or is at risk of having such. The instructions for the administration of the pharmaceutical composition may include information as to dosage, dosing schedule and routes of administration for the intended treatment.

According to an eleventh aspect of the present invention there is provided the p75NTR(NBP) according to the first, second or seventh aspect or the preferred embodiments thereof, or the nucleic acid molecule or vector according to the third and fourth aspects or the pharmaceutical composition of the ninth aspect for use in any one or more of the prevention or treatment or for ameliorating, controlling, reducing incidence of, or delaying the development or progression of a condition or the symptoms of a condition associated with any one or more of the neurotrophins NGF, BDNF, NT-3, NT-4/5.

NGF (Nerve growth factor) binds with at least two classes of receptors: the p75NTR and TrkA, a transmembrane tyrosine kinase, it is involved in axonal growth, branching and elongation. Conditions and symptoms associated with NGF are known. NGF is expressed in and associated with inflammatory conditions and pain [Protein Sequence NP_002497.2, NP_038637]. Also, NGF has been shown to play a role in number cardiovascular diseases, such as coronary atherosclerosis, obesity, type 2 diabetes, and metabolic syndrome as well as in Multiple Sclerosis. Reduced plasma levels of NGF (and also of BDNF) have been associated with acute coronary syndromes and metabolic syndromes. NGF is also related to various psychiatric disorders, such as dementia, depression, schizophrenia, autism, Rett syndrome, anorexia nervosa, and bulimia nervosa and has also been implicated in development of Alzheimer's disease and neurodegenerative disorders. NGF has also been shown to accelerate wound healing and there is evidence that it could be useful in the treatment of skin ulcers and corneal ulcers, it has been shown to reduce neural degeneration and to promote peripheral nerve regeneration in rats.

BDNF (brain-derived neurotrophic factor) is a neurotrophin which supports neuronal survival and growth during development of the nervous system [Protein Sequence NP_001137277.1, NP_001041604]. BDNF binds cell surface receptors TrkB and p75NTR and also modulates the activity of Alpha-7 nicotinic receptor. Conditions and symptoms associated with BDNF are known. BDNF has been shown to play a significant role in the transmission of physiologic and pathologic pain, particularly in models of acute pain, inflammatory pain and neuropathic pain, where BDNF synthesis is found to be greatly increased; also BDNF has been shown to be up-regulated in conditions of chronic pain as well as further conditions such as eczema and psoriasis. Down-regulation of BDNF is seen in depression, schizophrenia, obsessive-compulsive disorder, Alzheimer's disease, Huntington's disease, Rett syndrome, and dementia, as well as anorexia nervosa and bulimia nervosa.

Neurotrophin-4 (NT-4), also known as neurotrophin-5 (NT-5), is a neurotrophic factor that signals predominantly through the p75NTR and TrkB receptors and promotes the survival of peripheral sensory sympathetic neurons. The mature peptide of this protein is identical in all mammals examined including human, pig, rat and mouse. [Protein Sequence NP_006170, NP_937833]. NT-4 is synthesized by most neurons of the dorsal root ganglion (DRG) and those in the paravertebral and prevertebral sympathetic ganglia, spinal dorsal and ventral horn and is found expressed in many tissues including the prostate, thymus, placenta and skeletal muscle. Conditions and symptoms associated with NT-4/5 are known. Defects in NT4/5 are associated with susceptibility to primary open angle glaucoma. Neurotrophin 4 has also been shown to contribute to breast cancer cell survival and is a target to inhibit tumour growth. NT-4/5 is known to be involved in pain-signalling systems such as nociceptive pain, upregulation of NT-4/5 is also seen in chronic inflammatory conditions of the skin, such as dermatitis, eczema, prurigo lesions of atopic dermatitis. Down regulation of NT-4/5 is seen in Alzheimer's Disease, Huntington's disease.

Neurotrophin-3 (NT-3), is a neurotrophin that is structurally related to beta-NGF, BDNF, and NT-4, and that controls survival and differentiation of mammalian neurons and the maintenance of the adult nervous system, and may affect development of neurons in the embryo when it is expressed in human placenta. Conditions and symptoms associated with NT3 are known. NTF3-deficient mice generated by gene targeting display severe movement defects of the limbs. NT-3 signals through the Trk receptors and promotes the growth and survival of nerve and glial cells [Protein Sequence NP_001096124.1 and NP_032768]. The amino acid sequences of human, Mouse and rat NT-3 are identical. NT3 and its cognate receptor, tyrosine kinase C (TrkC), are known to modulate neuropathic pain and nociceptive pain and the mechanism of nociception and proprioception, for example NT3 expression is increased in the small DRG cells of neuropathic animals. NT3 expression is also associated with neuropathies such as diabetic polyneuropathy and HIV-related neuropathy, large fiber neuropathy including atrophy, it is further involved in the development of hyperalgesia (a decrease in the threshold of a normally noxious stimuli), allodynia (a non-noxious stimulus becomes noxious), and spontaneous pain (pain in the apparent absence stimuli) and is a known modulator of muscle pain.

The invention will now be described by reference to the following examples which are provided to illustrate, but not to limit, the invention.

The following Examples are provide to illustrate not to limit the invention.

EXAMPLES

Example 1. Endogenous p75NTR(NBP)-Neurotrophic Complex is Detected to Human Plasma An assay utilizing magnetic bead based NGF (Millipore Corp; MA) and immunoprecipitation using biotinylated goat polyclonal anti-human NGF antibody (Novus Biologicals; CO) followed by SISCAPA then subsequently determined in LC-MS/MS 5 (LLOQ 7 pg/ml) was employed to provide direct evidence for the existence of a p75NTR/NGF complex in human plasma. The polyclonal anti-NGF antibody, was used to quantify free NGF in human serum/plasma.

Peptide sequences (CAYGYYQDETTGR (SEQ ID NO. 4) VCEAGSGLVFSCQDK (SEQ ID NO. 6) WADAECEE-IPGR (SEQ ID NO. 7)) of the extracellular domain of p75NTR (as shown in FIG. 2) were selected as p75NTR standards by LC-MS/MS following chimera digestion of p75NTR. Co-immunoprecipitation of p75NTR detected in the total NGF assay (as described above) was able to demonstrate the presence of the p75NTR control peptides providing evidence of a soluble p75-NGF complex in human serum. Similar interactions of p75NTR(NBP) and BDNF, NT-3 and NT4/5 were also determined using co-immuno-precipitation with respective BDNF, NT-3 and NT4/5 antibodies. These studies demonstrate the presence of a soluble p75 neurotrophic binding protein in the plasma of humans bound to either NGF, BDNF, NT-3 and NT4/5.

The data presented in FIG. 2 shows soluble p75NTR (NBP) peptide standard fragments and co-immunoprecipitation of p75NTR(NBP) and NGF demonstrating p75NTR (NBP)-NGF complex in human plasma. It is evident from the findings of p75NTR(NBP)-NGF co-immunoprecipitation studies in human plasma, that the key peptides involved in binding in the neurotrophin-p75NTR(NBP) complex are: WADAECEEIPGR (SEQ ID NO. 7), CAYGYYQDETTGR (SEQ ID NO. 4), VCEAGSGLVFSCQDK (SEQ ID NO. 6), additionally we have determined that the sequence LDS-VTSDVVSATEPCKP (SEQ ID NO. 8) is also important in binding.

The experiments were repeated with BDNF and NT-3 showing the importance of the same key binding regions of p75NTR(NBP) and demonstrating the co-immunoprecipitation of p75NTR(NBP) with BDNF and NT-3 demonstrating p75NTR(NBP)-BDNF and p75NTR(NBP)-NT-3 complexes in human plasma.

Example 2. Soluble p75NTR(NBP) Inhibits NGF Function in U20S Cell Line Expressing TrkA and in U20S Cell Line Co-Expressing TrkA and p75NTR The effects of p75NTR(NBP) on NGF function was explored in U20S cells expressing TrkA and U20S cells co-expressing TrkA and p75NTR (Discoverx Corp CA). The assay was run in accordance with the PathHunter methodology (Discoverx Corp CA) briefly, U20S cells expressing TrkA and TrkA+p75NTR were purchased from DiscoveRx Corporation. The U20S cells expressing TrkA and cells co-expressing TrkA+p75NTR were plated in minimum essential medium (MEM; Sigma Aldrich)+0.5% horse serum (Sigma Aldrich) at a density of 40,000 cells/well and incubate at 37° C. over night. The plates were removed from the incubator 30 min prior to use and stored at room temperature.

NGFα (Sigma Aldrich) and p75NTR(NBP)-Fc (p75NTR (NBP) SEQ ID NO. 2 couple to IgG-Fc SEQ ID NO. 12 using linker SEQ ID NO 17) or p75NTR(NBP) (p75NTR (NBP) SEQ ID NO. 2) or p75NTR(NBP) coupled to albumin, SEQ ID NO. 10, or p75NTR(NBP) (p75NTR(NBP) SEQ ID NO. 2) coupled to transferrin, SEQ ID NO. 9, were diluted in Hanks Balanced Salt Solution Buffer (HBSS Sigma Aldrich) plus 0.25% BSA. NGF was serially diluted to give concentrations ranging from 0 nM to 200 nM. P75NTR(NBP) coupled to either Fc IgG, albumin or transferrin was diluted in HBSS to give a concentration of p75NTR of 100 ng/ml.

5 μl of each of the NGF concentrations (0-200 nM) and 5 μl of p75NTR(NBP)+/−carrier were added to each well. In an attempt to understand the impact on pre-incubation p75NTR(NBP)+/−carrier and NGF were allowed to incubate at room temperature for 20 minutes prior to adding 10 μl of this mixture to each well. Immediately following the addition of NGF and p75NTR(NBP)+/−carrier 12 μl of detection solution (Discoverx Corp CA) was added to each well and the plate was allowed to incubate at room temperature for 60 minutes prior to reading on a Parkard Victor 2 plate reader. Dose response curves and shifts in the curves in response to the addition of p75NTR(NBP) were observed. Regardless of the carrier used p75NTR(NBP) without a carrier, p75NTR(NBP)-Fc, p75NTR(NBP)-albumin or p75NTR(NBP)-transferrin suppression and shifts in the NGF dose response curves were observed (see FIG. 4).

Example 3. p75NTR(NBP) Inhibits BDNF Function in U20S Cell Line Expressing TrkB and in U20S Cell Line Co-Expressing TrkB and p75NTR The effects of p75NTR(NBP) on BDNF function was explored in U20S cells expressing TrkB and U20S cells co-expressing TrkB and p75NTR (Discoverx Corp CA). The assay was run in accordance with the PathHunter methodology (Discoverx Corp CA) briefly, U20S cells expressing TrkB and TrkB+p75NTR were purchased from DiscoveRx Corporation. The U20S cells expressing TrkB and cells co-expressing TrkB+p75NTR were plated in minimum essential medium (MEM; Sigma Aldrich)+0.5% horse serum (Sigma Aldrich) at a density of 40,000 cells/well and incubate at 37° C. overnight. The plate were removed from the incubator 30 minutes prior to use and stored at room temperature.

BDNFα (Sigma Aldrich) and p75NTR(NBP)-Fc (p75NTR(NBP) SEQ ID NO. 2 couple to IgG-Fc SEQ ID NO. 12 using linker SEQ ID NO 17) or p75NTR(NBP) (p75NTR(NBP) SEQ ID NO. 2) or p75NTR(NBP) coupled to albumin, SEQ ID NO. 10, or p75NTR(NBP) (p75NTR (NBP) SEQ ID NO. 2) coupled to transferrin, SEQ ID NO. 9, were diluted in Hanks Balanced Salt Solution Buffer (HBSS Sigma Aldrich) plus 0.25% BSA. BDNF was serially diluted to give concentrations ranging from 0 nM to 200 nM. P75NTR(NBP) coupled to either Fc-IgG, albumin or transferrin was diluted in HBSS to give a concentration of p75NTR(NBP) 100 ng/ml.

5 µl of each of the BDNF concentrations (0-200 nM) and 5 µl of p75NTR(NBP)+/−carrier were added to each well. In an attempt to understand the impact on pre-incubation p75NTR(NBP)+/−carrier and BDNF were allowed to incubate at room temperature for 20 minutes prior to adding 10 µl of this mixture to each well Immediately following the addition of BDNF and p75NTR(NBP)+/−carrier 12 µl of detection solution (Discoverx Corp CA) was added to each well and the plate was allowed to incubate at room temperature for 60 minutes prior to reading on a Parkard Victor 2 plate reader. Dose response curves and shifts in the curves in response to the addition of p75NTR(NBP) were observed. Regardless of the carrier used p75NTR(NBP) without a carrier, p75NTR(NBP)-Fc, p75NTR(NBP)-albumin or p75NTR(NBP)-transferrin suppression and shifts in the BDNF dose response curves were observed (see FIG. 5).

Example 4

Biocore data demonstrating p75NTR(NBP) binding to BDNF and competition between anti-BDNF and p75NTR (NBP). P75-Fc (p75NTR(NBP)-Fc), (500 µg/ml) was diluted to a concentration of 25 µg/ml in 10 mM acetate pH 5.0 and immobilised on the Biocore chip utilising the running buffer HBS-P (0.005% P20)+1 mg/ml BSA. A stock solution of BDNF (from R and D systems) 2 uM in HBS-P (0.005% P20)+1 mg/ml BSA buffer was prepared. BDNF competition experiment was preformed with p75 and presence or absence of MAB248 (BDNF anti-body RandD systems) at the following concentrations: i) MAB248 (500 nM) alone, ii) BDNF (20 nM)+MAB248 (500 nM) iii) BDNF (20 nM) alone and iv) BDNF (20 nM)+MAB248 (100 nM). All samples were prepared from stock solutions and diluted in running buffer; HBS-P (0.005% P20)+1 mg/ml BSA. All samples were left at room temperature for 30 minutes prior to injection. A manual sensorgram was initiated across the biocore chip at a flow rate of 50 ul/min. Each sample was injected for 30 seconds in the order listed above in a separate sensorgram cycle. Regeneration was carried out where necessary with 5 mM NaOH for 12 seconds (10 ul) cycle. As depicted in FIG. 6 p75NTR(NBP) binds BDNF.

Example 5. p75NTR(NBP) Inhibition of NGF Activity in PC12 Cells

The p75NTR(NBP) was demonstrated to significantly inhibit the activity of NGF in PC-12 and N2OS cells expressing TrkA and/or TrkA plus p75 on the cell surface, FIG. 7.

Low-passage PC12 cells (passage number 20-24) were grown directly on 96-well plates in Dulbecco's modified Eagle's medium (DMEM) supplemented with 5% fetal bovine serum and 10% heat-inactivated horse serum and penicillin-streptomycin (10 U/ml-0.1 mg/ml), and incubated in a humidified atmosphere containing 5% $CO_2$, 37° C. NGF (50 ng/ml) was added to the growth medium to differentiate the PC12 cells. A dose concentration of P75NTR(NBP) of 200, 100, 50, 25, 12.5, 6.25, 3.1, 1.5, 0.78, 0.39, 0.2, 0.1 ng/ml was added to each well across the plate. The plate was incubated at 37° C. for 24 hours following which the cell numbers were determined by a cell counter. As shown in FIG. 8 the addition of p75NTR(NBP) to the media blocked significantly the differentiation of PC-12 cells to their axonal phenotype. In the presence of NGF PC-12 cells differentiate and form a neuronal like phenotype. This was inhibited in a dose dependent manner in response to p75NTR(NBP). It was concluded from these studies that p75NTR(NBP) blocks the action of NGF.

Example 6. Neurotrophic Binding Protein p75NTR(NBP) Inhibits BDNF Effect in Mechanical Hyperalgesia in a Model of Nerve Excitability Male Sprague Dawley rats were anaesthetised with isoflurane (5% in oxygen for induction, 1.5-2.0% in oxygen for maintenance). The spinal cord was exposed by lumbar laminectomy to uncover the L4-L6 region of the cord, and a tungsten microelectrode inserted into the dorsal horn to record from an isolated wide dynamic range neurone. Individual WDR neurones were isolated such that the spike amplitude of the recorded unit was at least 3× the level of the baseline noise. Responses were amplified using a neurolog AC-coupled amplifier and recorded using CED spike2 software. Prior to drug application, 3 stable baseline responses (<10% variation) were obtained to a range of natural stimuli (brush, von Frey, pinch and heat). Brush stimulus was applied by stroking the centre of the peripheral receptive field with a fine cotton wisp. Von Frey filament and heat (using a constant water jet set at 43 degrees) were applied for a period of 10 seconds. Pinch was applied for a period of 5 seconds. Once stable baseline responses were obtained, BDNF alone (500 ng in 0.1% BSA) or BDNF (500 ng)+ p75NTR(NBP) (500 ng pre-incubated for 40 minutes prior to injection) was applied to the centre of the receptive field in a volume of 25 ul using an insulin syringe. Drug effects were followed for 150 minutes and tests carried out at 10 min intervals. At the termination of the experiment the rat was culled by cervical dislocation.

As demonstrated in FIG. 8 BDNF caused a significant increase in neuronal excitability and this was amplified following stimulus. The addition of p75NTR(NBP) significant reduced neuronal excitability in response to all stimulus; saline, BDNF, brush and pinch. It is evident that p75NTR(NBP) reduces neuronal excitability and subsequently pain.

Example 7—Neurotrophic Binding Protein P75NTR(NBP) Inhibits Hyperalgesia in UVIH Model Exposure of Animals to UV Charles River male Sprague Dawley rats (175-200 g) were anaesthetised with a 2% isofluorane $O_2$ mixture. Anaesthesia was maintained via a nose cone while the plantar surface of the right hind paw was irradiated with 300 mJ/cm$^2$ of UV (Saalmann CupCube system, Saalmann GmbH, Germany; $\lambda$=280-400 nm). The source of irradiation was adapted to the plantar surface of rat's hind paw by using shaped delivery collar (8×12 mm), attached to the UV source (Pfizer Facilities Management and Engineering Team). Intensity of UV sources was calibrated using the ABLE 1400A radiometer with SEL005/WBS320/TD Filter (ABLE Instruments and Controls Ltd). The UV exposure used, causes cutaneous erythema in naïve rats and no other adverse events (no loss in body weight, no sign of stress or obvious discomfort).

Evaluation of Thermal Hyperalgesia

Thermal hyperalgesia was assessed using the rat plantar test (Ugo Basile, Italy) following a modified method of Hargreaves et al (1988). Rats were habituated to the apparatus (15-30 min) before testing. The plantar test consisted of three individual perspex boxes on an elevated glass table. Two rats were housed in each box so that 6 rats/apparatus can be tested simultaneously.

A mobile infrared heat source was applied directly below the plantar surface of the rat hind paw. The paw withdrawal latency (PWL) was defined as the time (seconds) taken by the rat to remove its hind paw from the heat source. The source was calibrated to give an response of 8-12 sec on untreated animals (105-120 mW/cm$^2$). An automatic cut off point of 20 sec was set to prevent tissue damage.

Five recordings were taken from each rat hind paws during baselines measurements (naïve rats before UV exposures, Day 0) and confirmation of hyperalgesia onset (days 1). Two sessions per day were performed on day 0 and 1.

Three recordings per paw were instead collected for baselines and each testing point during evaluation of efficacy of medicaments on day 2, 3 and 4 (48, 72 and 96 hours post UV exposure, respectively). Uninjured paw was always assessed first.

Thermal hyperalgesia is defined as animals showing mean PWL≤5 sec, which are selected for studies.

Evaluation of Static Allodynia

Animals are habituated to wire bottom test cages prior to the assessment of allodynia. Animals are familiarised with the von Frey Hairs by application of 15 g, 8 g+4 g filament on 1$^{st}$ day of habituation, 4 g filament 2$^{nd}$ day before a full up down measurement is performed. Static allodynia is evaluated by application of von Frey hairs (Stoelting, Wood Dale, Ill., U.S.A.) in ascending order of force (0.6, 1, 1.4, 2, 4, 6, 8, 10, 15 and 26 grams) to the plantar surface of hind paws. Each von Frey hair is applied to the paw for a maximum of 6 seconds, or until a withdrawal response occurs. Once a withdrawal response to a von Frey hair is established, the paw is re-tested, starting with the filament below the one that produced a withdrawal, and subsequently with the remaining filaments in descending force sequence until no withdrawal occurs. The highest force of 26 g lifts the paw as well as eliciting a response, thus representing the cut off point. Each animal has both hind paws tested in this manner. The lowest amount of force required to elicit a response is recorded as paw withdrawal threshold (PWT) in grams. Static allodynia is defined as present if animals respond to a stimulus of, or less than, 4 g, which is innocuous in normal rats.

Animals are baselined prior to testing and those displaying allodynia which meets the inclusion criteria are randomized based on PWL and are dosed. Test compound is dosed and at predetermined times (dependant on the pharmacokinetic properties of the test compound), following dosing measurements are made at selected times post dosing and all data is collected for analysis. As demonstrated in FIG. 9 PWL data for the p75NTR(NBP) 10 mg/kg subcutaneously (denoted NBPP-Fc) is shown in comparison to control, ibuprofen 100 mg/kg po and anti-NGF antibody 10 mg/kg subcutaneously, data for evaluation of thermal hyperalgesia showed equivalent measures in each case.

CITATIONS

Armour K L, Clark M R, Hadley A G, Williamson L M. 1999. Recombinant human IgG molecules lacking Fcgamma receptor I binding and monocyte triggering activities. Eur J Immunol. 29(8):2613-24.

Barthel C, Yeremenko N, Jacobs R, Schmidt R E, Bernateck M, Zeidler H, Tak P P, Baeten D, Rihl M. 2009. Nerve growth factor and receptor expression in rheumatoid arthritis and spondyloarthritis. Arthritis Res Ther. 11:R82.

Bothwell M A, Shooter E M. 1977. Dissociation equilibrium constant of beta nerve growth factor. J Biol Chem 252:8532-8536.

Chu C, Levine E, Gear R W, Bogen O, Levine J D. 2011. Mitochondrial dependence of nerve growth factor-induced mechanical hyperalgesia. Pain. 152:1832-7.

Cirillo G, Cavaliere C, Bianco M R, De Simone A, Colangelo A M, Sellitti S, Alberghina L, Papa M. 2010. Intrathecal NGF administration reduces reactive astrocytosis and changes neurotrophin receptors expression pattern in a rat model of neuropathic pain. Cell Mol Neurobiol. 30:51-62.

Cowan, W. M. 2001. Viktor Hamburger and Rita Levi-Montalcini: the path to the discovery of nerve growth factor. Annu. Rev. Neurosci. 24:551-600.

Fukui Y, Ohtori S, Yamashita M, Yamauchi K, Inoue G, Suzuki M, Orita S, Eguchi Y, Ochiai N, Kishida S, Takaso M, Wakai K, Hayashi Y, Aoki Y, Takahashi K. 2010. Low affinity NGF receptor (p75 neurotrophin receptor) inhibitory antibody reduces pain behavior and CGRP expression in DRG in the mouse sciatic nerve crush model. J Orthop Res. 2010; 28:279-83.

Ghilardi J R, Freeman K T, Jimenez-Andrade J M, Mantyh W G, Bloom A P, Bouhana K S, Trollinger D, Winkler J, Lee P, Andrews S W, Kuskowski M A, Mantyh P W. 2010. Sustained blockade of neurotrophin receptors TrkA, TrkB and TrkC reduces non-malignant skeletal pain but not the maintenance of sensory and sympathetic nerve fibers. Bone. 48:389-98.

Hayashi K, Ozaki N, Kawakita K, Itoh K, Mizumura K, Furukawa K, Yasui M, Hori K, Yi S Q, Yamaguchi T, Sugiura Y. 2011. Involvement of NGF in the Rat Model of Persistent Muscle Pain Associated With Taut Band. J Pain. 12:1059-68.

He X L, Garcia K C. 2004. Structure of nerve growth factor complexed with the shared neurotrophin receptor p75. Science 304:870-875.

Huang E J, Reichardt L F. 2003. Trk receptors: roles in neuronal signal transduction. Annu Rev Biochem. 72:609-42

Huang Y Z, Pan E, Xiong Z Q, McNamara J O. 2008. Zinc-mediated transactivation of TrkB potentiates the hippo-campal mossy fiber-CA3 pyramid synapse. Neuron 57:546-558.

Iwakura N, Ohtori S, Orita S, Yamashita M, Takahashi K, Kuniyoshi K. 2010. Role of low-affinity nerve growth factor receptor inhibitory antibody in reducing pain behavior and calcitonin gene-related Peptide expression in a rat model of wrist joint inflammatory pain. J Hand Surg Am. 35:267-73.

Johnson D, Lanahan A, Buck C R, Sehgal A, Morgan C, Mercer E, Bothwell M, et al. 1986. Expression and structure of the human NGF receptor. Cell 47:545-554.

Jung K M, Tan S, Landman N, Petrova K, Murray S, Lewis R, Kim P K, et al. 2003. Regulated intra-membrane proteolysis of the p75 neurotrophin receptor modulates its association with the TrkA receptor. J Biol Chem 278: 42161-42169.

Kanning K C, Hudson M, Amieux P S, Wiley J C, Bothwell M, Schecterson L C. 2003. Proteolytic processing of the p75 neurotrophin receptor and two homologs generates C-terminal fragments with signaling capability. J Neurosci 23:5425-5436.

Kenchappa R S, Zampieri N, Chao M V, Barker P A, Teng H K, Hempstead B L, Carter B D. 2006. Ligand-dependent cleavage of the P75 neurotrophin receptor is necessary for NRIF nuclear translocation and apoptosis in sympathetic neurons. Neuron 50:219-232.

McDonald C L, Bandtlow C, Reindl M. 2011. Targeting the Nogo receptor complex in diseases of the central nervous system. Curr Med Chem. 18:234-44.

Orita S, Ohtori S, Nagata M, Horii M, Yamashita M, Yamauchi K, Inoue G, Suzuki M, Eguchi Y, Kamoda H, Arai G, Ishikawa T, Miyagi M, Ochiai N, Kishida S, Takaso M, Aoki Y, Takahashi K. 2010. Inhibiting nerve growth factor or its receptors downregulates calcitonin gene-related peptide expression in rat lumbar dorsal root ganglia innervating injured intervertebral discs. J Orthop Res. December; 28:1614-20.

Pezet S, Onténiente B, Jullien J, Junier M P, Grannec G, Rudkin B B, Calvino B. 2010. Differential regulation of NGF receptors in primary sensory neurons by adjuvant-induced arthritis in the rat. Pain. 90:113-25.

Radeke M J, Misko T P, Hsu C, Herzenberg L A, Shooter E M. 1987. Gene transfer and molecular cloning of the rat nerve growth factor receptor. Nature 325:593-597.

Raychaudhuri S P, Raychaudhuri S K, Atkuri K R, Herzenberg L A, Herzenberg L A. 2011. Nerve growth factor: A key local regulator in the pathogenesis of inflammatory arthritis. Arthritis Rheum. 2011 Jul. 26.

Svensson P, Wang M W, Dong X D, Kumar U, Cairns B E. 2010. Human nerve growth factor sensitizes masseter muscle nociceptors in female rats. Pain. March; 148:473-80.

Tria M A, Fusco M, Vantini G, Mariot R. 1994. Pharmacokinetics of nerve growth factor (NGF) following different routes of administration to adult rats. Exp Neurol. 127(2):178-83

Truzzi F, Marconi A, Atzei P, Panza M C, Lotti R, Dallaglio K, Tiberio R, Palazzo E, Vaschieri C, Pincelli C. 2011. p75 neurotrophin receptor mediates apoptosis in transit-amplifying cells and its overexpression restores cell death in psoriatic keratinocytes. Cell Death Differ. June; 18:948-58.

Ueda K, Hirose M, Murata E, Takatori M, Ueda M, Ikeda H, Shigemi K. 2010. Local administration of a synthetic cell-penetrating peptide antagonizing TrkA function suppresses inflammatory pain in rats. J Pharmacol Sci.; 112:438-43.

Vilar M, Charalampopoulos I, Kenchappa R S, Reversi A, Klos-Applequist J M, Karaca E, Simi A, et al. 2009a. Ligand-independent signaling by disulfide-crosslinked dimers of the p75 neurotrophin receptor. J Cell Sci 122:3351-3357.

Vilar M, Charalampopoulos I, Kenchappa R S, Simi A, Karaca E, Reversi A, Choi S. 2009b. Activation of the p75 neurotrophin receptor through conformational rearrangement of disulphide-linked receptor dimers. Neuron 62:72-83.

Watanabe T, Ito T, Inoue G, Ohtori S, Kitajo K, Doya H, Takahashi K, Yamashita T. 2010. The p75 receptor is associated with inflammatory thermal hypersensitivity. J Neurosci Res. 2008 December; 86:3566-74

Yamaoka J, Di Z H, Sun W, Kawana S. 2007. Changes in cutaneous sensory nerve fibers induced by skin-scratching in mice. J Dermatol Sci. April; 46(1):41-51

The invention claimed is:

1. A kit comprising:
   (a) a p75NTR neurotrophin binding protein (p75NTR (NBP)) connected to one or more auxiliary molecules selected from the group consisting of transferrin or a portion thereof, albumin or a portion thereof, an immunoglobulin Fc or a portion thereof, and a polyethylene glycol polymer chain, wherein the p75NTR(NBP) binds to any of NGF, BDNF, NT3, or NT4/5 with a binding affinity ($K_d$) of between about 0.1 nM to about 50 nM as measured by surface plasmon resonance at 20° C.; and
   (b) instructions for the administration of an effective amount of the p75NTR(NBP) to an individual for treating pain and/or a symptom of pain in a subject in need thereof.

2. The kit of claim 1, wherein the p75NTR(NBP) is connected to the one or more auxiliary molecules via one or more linkers.

3. The kit of claim 2, wherein the linker is selected from:
   (a) a covalent bond,
   (b) a non-covalent bond,
   (c) a peptide bond, or
   (d) one amino acid or a plurality of amino acids comprising a peptide.

4. The kit of claim 1, wherein the p75NTR(NBP) is a human p75NTR(NBP).

5. The kit of claim 1, wherein the p75NTR(NBP) comprises one or more of neurotrophin binding domain 1 (SEQ ID NO:4), 2 (SEQ ID NO:5), 3 (SEQ ID NO:6), 4 (SEQ ID NO:7), or 5 (SEQ ID NO:8).

6. The kit of claim 1, wherein the p75NTR(NBP) comprises:
   (a) one or more of SEQ ID NO:4, SEQ ID NO:5, SEQ ID NO:6, SEQ ID NO:7, or SEQ ID NO:8;
   (b) SEQ ID NO:3 or a portion thereof comprising (a); or
   (c) SEQ ID NO:2 or a portion thereof comprising (a).

7. The kit of claim 1, wherein the p75NTR(NBP) is connected to more than one auxiliary molecule, optionally each auxiliary molecule is either the same, or different, or a mixture of the same and different.

8. The kit of claim 7, wherein the more than one auxiliary molecule comprises a multimer of auxiliary molecules linked to p75NTR(NBP) via a linker, and wherein each molecule may be the same or different or a mixture of the same and different.

9. The kit of claim 1, wherein the p75NTR(NBP) consists of:
   (a) a p75NTR(NBP) of sequence SEQ ID NO:3, and optionally
   (b) an immunoglobulin Fc, optionally wherein the immunoglobulin Fc is selected from SEQ ID NOs:12, 15, and 16, and further optionally
   (c) a linker, optionally wherein the linker is selected from SEQ ID NOs:17, 18, and 19.

10. The kit of claim 1, wherein the instructions recite methods of administration of an effective amount of the p75NTR(NBP) for treatment of pain or a symptom of pain, wherein the pain or symptom of pain is selected from:
    (a) acute pain and/or spontaneous pain,
    (b) chronic pain and or on-going pain,
    (c) inflammatory pain including any one of arthritic pain, pain resulting from osteoarthritis or rheumatoid arthritis, resulting from inflammatory bowel diseases,
    (d) nociceptive pain,
    (e) neuropathic pain, including painful diabetic neuropathy or pain associated with post-herpetic neuralgia,
    (f) hyperalgesia,
    (g) allodynia,
    (h) central pain, central post-stroke pain, pain resulting from multiple sclerosis, pain resulting from spinal cord injury, or pain resulting from Parkinson's disease or epilepsy,
    (i) cancer pain,
    (j) post-operative pain,
    (k) visceral pain, including digestive visceral pain and non-digestive visceral pain, pain due to gastrointestinal (GI) disorders, pain resulting from functional bowel disorders (FBD), pain resulting from inflammatory bowel diseases (IBD), pain resulting from dysmenorrhea, pelvic pain, cystitis, interstitial cystitis or pancreatitis,
    (l) musculo-skeletal pain, myalgia, fibromyalgia, spondylitis, sero-negative (non-rheumatoid) arthropathies, non-articular rheumatism, dystrophinopathy, Glycogenolysis, polymyositis, pyomyositis,
    (m) heart or vascular pain, pain due to angina, myocardial infarction, mitral stenosis, pericarditis, Raynaud's phenomenon, scleredoma, scleroderma, or skeletal muscle ischemia,
    (n) head pain including migraine, migraine with aura, migraine without aura cluster headache, tension-type headache,
    (o) orofacial pain, including dental pain, temporomandibular myofascial pain or tinnitus, or
    (p) back pain, bursitis, menstrual pain, migraine, referred pain, trigeminal neuralgia, hypersensitisation, pain resulting from spinal trauma and/or degeneration or stroke.

11. The kit of claim 1, wherein the p75NTR neurotrophin binding protein further comprises a pharmaceutical composition including a pharmaceutically acceptable carrier and/or an excipient.

12. The kit of claim 1, further comprising a second pharmacologically active compound.

13. The kit of claim 12, wherein the second pharmacologically active compound is selected from: an opioid analgesic, a nonsteroidal anti-inflammatory drug (NSAID), a barbiturate sedative, a benzodiazepine having a sedative action, an H1 antagonist having a sedative action, a sedative, a skeletal muscle relaxant, an NMDA receptor antagonist, an alpha-adrenergic, a tricyclic antidepressant, an anticonvulsant, a tachykinin (NK) antagonist, a muscarinic antagonist, a COX-2 selective inhibitor, a coal-tar analgesic, a neuroleptic, a vanilloid receptor agonist, a beta-adrenergic, a corticosteroid, a 5-HT receptor agonist or antagonist, a 5-HT2A receptor antagonist, a cholinergic (nicotinic) analgesic, Tramadol, a PDEV inhibitor, a cannabinoid; a metabotropic glutamate subtype 1 receptor (mGluR1) antagonist, a serotonin reuptake inhibitor, a noradrenaline (norepinephrine) reuptake inhibitor, a dual serotonin-noradrenaline reuptake inhibitor, an inducible nitric oxide synthase (iNOS) inhibitor, an acetylcholinesterase inhibitor, a prostaglandin E2 subtype 4 (EP4) antagonist, a leukotriene B4 antagonist, a 5-lipoxygenase inhibitor, a sodium channel blocker, or a 5-HT3 antagonist, and the pharmaceutically acceptable salts and solvates thereof.

* * * * *

SEQUENCE LISTING

```
<160> NUMBER OF SEQ ID NOS: 19

<210> SEQ ID NO 1
<211> LENGTH: 427
<212> TYPE: PRT
<213> ORGANISM: Homo sapiens

<400> SEQUENCE: 1

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60
```

-continued

Glu Pro Cys Leu Asp Ser Val Thr Phe Ser Asp Val Val Ser Ala Thr
 65                  70                  75                  80

Glu Pro Cys Lys Pro Cys Thr Glu Cys Val Gly Leu Gln Ser Met Ser
             85                  90                  95

Ala Pro Cys Val Glu Ala Asp Ala Val Cys Arg Cys Ala Tyr Gly
        100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Glu Gly Glu Lys Leu His Ser Asp
290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 2
<211> LENGTH: 250
<212> TYPE: PRT
<213> ORGANISM: Homo sapiens

<400> SEQUENCE: 2

Met Gly Ala Gly Ala Thr Gly Arg Ala Met Asp Gly Pro Arg Leu Leu
1               5                   10                  15

```
Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
 50                  55                  60

Glu Pro Cys Leu Asp Ser Val Thr Phe Ser Asp Val Val Ser Ala Thr
 65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn
                245                 250

<210> SEQ ID NO 3
<211> LENGTH: 221
<212> TYPE: PRT
<213> ORGANISM: Homo sapiens

<400> SEQUENCE: 3

Lys Glu Ala Cys Pro Thr Gly Leu Tyr Thr His Ser Gly Glu Cys Cys
 1               5                  10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
 50                  55                  60

Gln Ser Met Ser Ala Pro Cys Val Glu Ala Asp Asp Ala Val Cys Arg
 65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Gly Thr Tyr Ser Asp Glu
        115                 120                 125

Ala Asn His Val Asp Pro Cys Leu Pro Cys Thr Val Cys Glu Asp Thr
```

```
                130                 135                 140
Glu Arg Gln Leu Arg Glu Cys Thr Arg Trp Ala Asp Ala Glu Cys Glu
145                 150                 155                 160

Glu Ile Pro Gly Arg Trp Ile Thr Arg Ser Thr Pro Pro Glu Gly Ser
                165                 170                 175

Asp Ser Thr Ala Pro Ser Thr Gln Glu Pro Glu Ala Pro Pro Glu Gln
                180                 185                 190

Asp Leu Ile Ala Ser Thr Val Ala Gly Val Val Thr Thr Val Met Gly
            195                 200                 205

Ser Ser Gln Pro Val Val Thr Arg Gly Thr Thr Asp Asn
        210                 215                 220

<210> SEQ ID NO 4
<211> LENGTH: 13
<212> TYPE: PRT
<213> ORGANISM: Homo sapiens

<400> SEQUENCE: 4

Cys Ala Tyr Gly Tyr Tyr Gln Asp Glu Thr Thr Gly Arg
1               5                   10

<210> SEQ ID NO 5
<211> LENGTH: 49
<212> TYPE: PRT
<213> ORGANISM: Homo sapiens

<400> SEQUENCE: 5

Val Cys Glu Ala Gly Ser Gly Leu Val Phe Ser Cys Gln Asp Lys Gln
1               5                   10                  15

Asn Thr Val Cys Glu Glu Cys Pro Gly Gly Thr Tyr Ser Asp Glu Ala
                20                  25                  30

Asn His Val Asp Pro Cys Leu Pro Cys Thr Val Cys Glu Asp Thr Glu
            35                  40                  45

Arg

<210> SEQ ID NO 6
<211> LENGTH: 15
<212> TYPE: PRT
<213> ORGANISM: Homo sapiens

<400> SEQUENCE: 6

Val Cys Glu Ala Gly Ser Gly Leu Val Phe Ser Cys Gln Asp Lys
1               5                   10                  15

<210> SEQ ID NO 7
<211> LENGTH: 12
<212> TYPE: PRT
<213> ORGANISM: Homo sapiens

<400> SEQUENCE: 7

Trp Ala Asp Ala Glu Cys Glu Glu Ile Pro Gly Arg
1               5                   10

<210> SEQ ID NO 8
<211> LENGTH: 17
<212> TYPE: PRT
<213> ORGANISM: Homo sapiens

<400> SEQUENCE: 8

Leu Asp Ser Val Thr Ser Asp Val Val Ser Ala Thr Glu Pro Cys Lys
1               5                   10                  15
```

Pro

<210> SEQ ID NO 9
<211> LENGTH: 698
<212> TYPE: PRT
<213> ORGANISM: Homo sapiens

<400> SEQUENCE: 9

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
          370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
                420                 425                 430

Lys Ser Asp Asn Cys Glu Asp Thr Pro Glu Ala Gly Tyr Phe Ala Val
                435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
    515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
                580                 585                 590

Tyr Ala Asn Cys His Leu Ala Arg Ala Pro Asn His Ala Val Val Thr
                595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
                660                 665                 670

Glu Tyr Val Lys Ala Val Gly Asn Leu Arg Lys Cys Ser Thr Ser Ser
                675                 680                 685

Leu Leu Glu Ala Cys Thr Phe Arg Arg Pro
    690                 695

<210> SEQ ID NO 10
<211> LENGTH: 609
<212> TYPE: PRT
<213> ORGANISM: Homo sapiens

<400> SEQUENCE: 10

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu

```
            35                  40                  45
Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                     85                  90                  95

Lys Leu Cys Thr Val Ala Thr Leu Arg Glu Thr Tyr Gly Glu Met Ala
                    100                 105                 110

Asp Cys Cys Ala Lys Gln Glu Pro Glu Arg Asn Glu Cys Phe Leu Gln
                115                 120                 125

His Lys Asp Asp Asn Pro Asn Leu Pro Arg Leu Val Arg Pro Glu Val
            130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                    165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                    245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                    325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                    405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
450                 455                 460
```

```
Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 11
<211> LENGTH: 212
<212> TYPE: PRT
<213> ORGANISM: Homo sapiens

<400> SEQUENCE: 11

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asp Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210
```

<210> SEQ ID NO 12
<211> LENGTH: 326
<212> TYPE: PRT
<213> ORGANISM: Homo sapiens

<400> SEQUENCE: 12

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 13
<211> LENGTH: 165
<212> TYPE: PRT
<213> ORGANISM: Homo sapiens

<400> SEQUENCE: 13

Cys Tyr Thr Leu Leu Leu Thr Thr Pro Ser Trp Val Leu Ser Gln
1               5                   10                  15

Val Thr Leu Lys Glu Ser Gly Pro Val Leu Val Lys Pro Thr Glu Thr
                20                  25                  30

Leu Thr Leu Thr Cys Thr Val Ser Gly Phe Ser Leu Ser Asn Ala Lys
            35                  40                  45

Met Gly Val Ser Trp Ile Arg Gln Pro Pro Gly Lys Ala Leu Glu Trp
    50                  55                  60

Leu Ala His Ile Phe Ser Asn Asp Glu Lys Ser Tyr Ser Thr Ser Leu
65                  70                  75                  80

Lys Ser Arg Leu Thr Ile Ser Lys Asp Thr Ser Lys Ser Gln Val Val
                85                  90                  95

Leu Thr Met Thr Asn Met Asp Pro Val Asp Thr Ala Thr Tyr Tyr Cys
            100                 105                 110

Ala Arg Ile Phe Thr Ile Thr Tyr Ser Asn Tyr Val Leu Gln Tyr Tyr
        115                 120                 125

Tyr Tyr Met Asp Val Trp Gly Lys Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Gly Gly
                165

<210> SEQ ID NO 14
<211> LENGTH: 217
<212> TYPE: PRT
<213> ORGANISM: Homo sapiens

<400> SEQUENCE: 14

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Glu Gly Asn Val
            180                 185                 190

Phe Ser Cys Ser Val Met His Glu Ala Leu His Asn His Tyr Thr Gln

Lys Ser Leu Ser Leu Ser Leu Gly Lys
            210                 215

<210> SEQ ID NO 15
<211> LENGTH: 209
<212> TYPE: PRT
<213> ORGANISM: Homo sapiens

<400> SEQUENCE: 15

Gly Gly Pro Ser Val Phe Leu Phe Pro Pro Lys Pro Lys Asp Thr Leu
1               5                   10                  15

Tyr Ile Thr Arg Glu Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Asp Glu Leu Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser

<210> SEQ ID NO 16
<211> LENGTH: 225
<212> TYPE: PRT
<213> ORGANISM: Homo sapiens

<400> SEQUENCE: 16

Thr His Thr Cys Pro Pro Cys Pro Ala Pro Glu Phe Glu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

```
Tyr Lys Cys Lys Val Ser Asn Lys Ala Leu Pro Ala Ser Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 17
<211> LENGTH: 5
<212> TYPE: PRT
<213> ORGANISM: Artificial
<220> FEATURE:
<223> OTHER INFORMATION: Linker sequence
<220> FEATURE:
<221> NAME/KEY: MISC_FEATURE
<222> LOCATION: (1)..(5)
<223> OTHER INFORMATION: (GGGGS)n (n = 3 to 4)

<400> SEQUENCE: 17

Gly Gly Gly Gly Ser
1               5

<210> SEQ ID NO 18
<211> LENGTH: 5
<212> TYPE: PRT
<213> ORGANISM: Artificial
<220> FEATURE:
<223> OTHER INFORMATION: Linker sequence
<220> FEATURE:
<221> NAME/KEY: MISC_FEATURE
<222> LOCATION: (1)..(5)
<223> OTHER INFORMATION: (EAAAK)n (n = 2 to 5)

<400> SEQUENCE: 18

Glu Ala Ala Ala Lys
1               5

<210> SEQ ID NO 19
<211> LENGTH: 5
<212> TYPE: PRT
<213> ORGANISM: Artificial
<220> FEATURE:
<223> OTHER INFORMATION: Linker sequence

<400> SEQUENCE: 19

Gly Gly Gly Gly Ser
1               5
```